US009194779B2

(12) United States Patent
Williamson, IV et al.

(10) Patent No.: US 9,194,779 B2
(45) Date of Patent: Nov. 24, 2015

(54) METHOD FOR AUTOMATED PROCESSING AND EMBEDDING OF TISSUE SAMPLES

(71) Applicant: BioPath Automation, L.L.C., Loveland, OH (US)

(72) Inventors: Warren P. Williamson, IV, Loveland, OH (US); Stephen P. Whitlatch, Cincinnati, OH (US)

(73) Assignee: BioPath Automation, L.L.C., Loveland, OH (US)

( * ) Notice: Subject to any disclaimer, the term of this patent is extended or adjusted under 35 U.S.C. 154(b) by 0 days.

(21) Appl. No.: 14/643,136

(22) Filed: Mar. 10, 2015

(65) Prior Publication Data
US 2015/0198509 A1    Jul. 16, 2015

Related U.S. Application Data

(60) Continuation of application No. 14/286,271, filed on May 23, 2014, now Pat. No. 8,999,270, which is a continuation of application No. 13/047,044, filed on Mar. 14, 2011, now Pat. No. 8,734,735, which is a division of application No. 12/696,506, filed on Jan. 29, 2010, now abandoned, which is a division of application No. 11/010,773, filed on Dec. 13, 2004, now Pat. No. 7,722,810, which is a continuation of application No. PCT/US02/30779, filed on Sep. 26, 2002.

(51) Int. Cl.
*A61B 10/00* (2006.01)
*G01N 1/36* (2006.01)
*G01N 35/00* (2006.01)

(52) U.S. Cl.
CPC ............ *G01N 1/36* (2013.01); *G01N 35/00732* (2013.01); *G01N 2001/366* (2013.01); *Y10T 436/2525* (2015.01); *Y10T 436/2575* (2015.01)

(58) Field of Classification Search
CPC ........................................................ G01N 1/36
See application file for complete search history.

(56) References Cited

U.S. PATENT DOCUMENTS 7,156,814 B1 *  1/2007  Williamson, IV et al. ... 600/562

* cited by examiner

*Primary Examiner* — Jyoti Nagpaul
(74) *Attorney, Agent, or Firm* — Wood, Herron & Evans, LLP

(57) ABSTRACT

An automated machine for handling and embedding tissue samples contained on microtome sectionable supports. The machine includes an input member configured to hold a plurality of the microtome sectionable supports prior to a tissue embedding operation. An output member is configured to hold a plurality of the microtome sectionable supports after the tissue embedding operation. A cooling unit is configured to hold at least one of the microtome sectionable supports during the tissue embedding operation. A motorized carrier assembly is mounted for movement and configured to hold at least one of the microtome sectionable supports. The carrier assembly moves the support from the input member to the cooling unit and, finally, to the output member. A dispensing device dispenses an embedding material onto the microtome sectionable support and at least one tissue sample carried by the microtome sectionable support during the embedding operation.

10 Claims, 27 Drawing Sheets

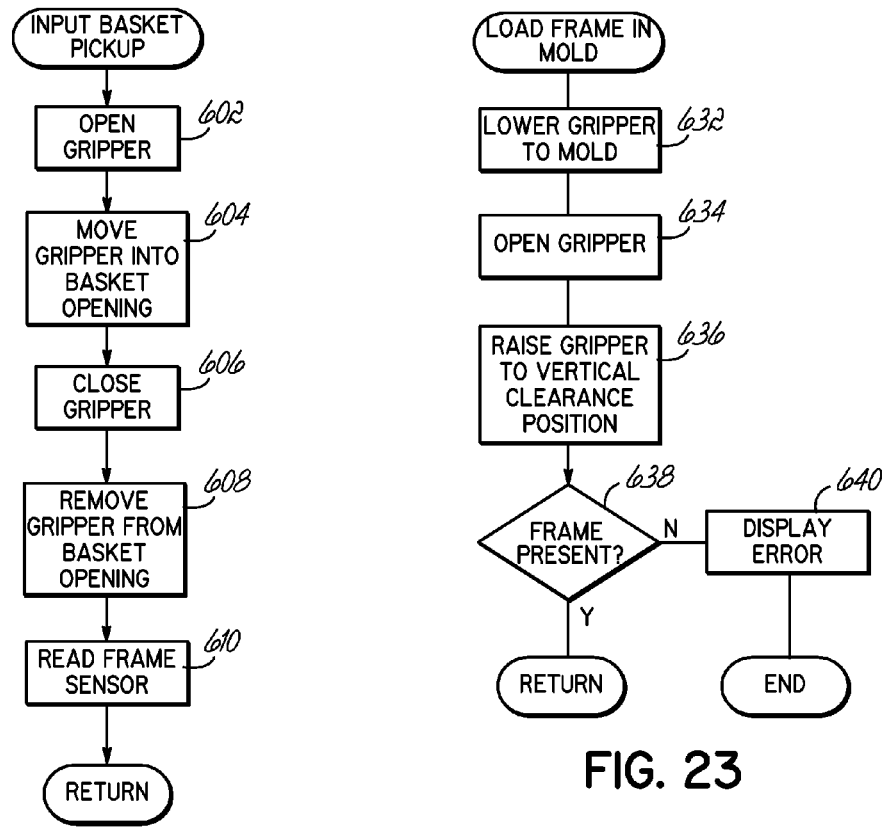
FIG. 21
FIG. 23
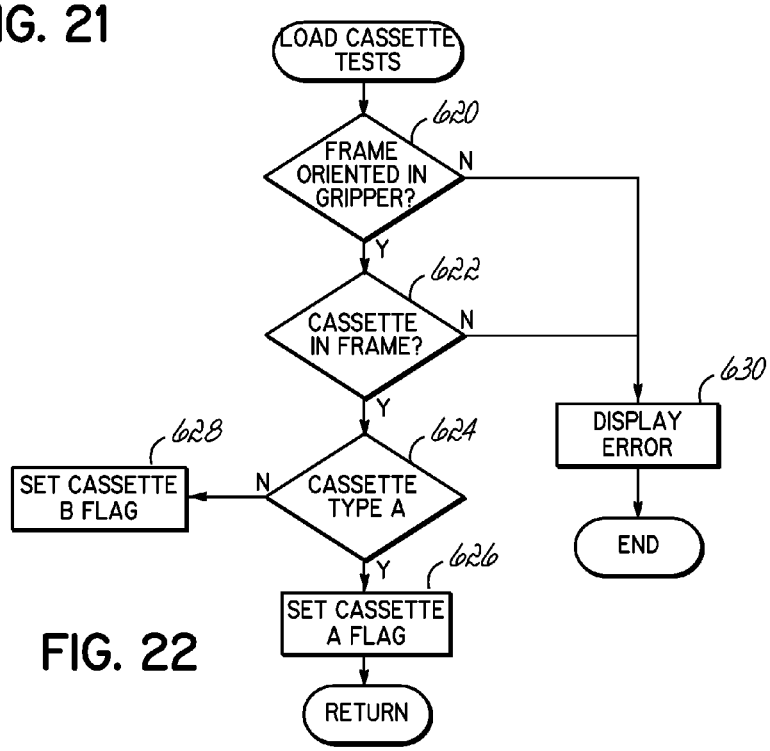
FIG. 22

METHOD FOR AUTOMATED PROCESSING AND EMBEDDING OF TISSUE SAMPLES

CROSS REFERENCE TO RELATED APPLICATIONS

The present application is a continuation of application Ser. No. 14/286,271, filed May 23, 2014 (pending) which is a continuation of application Ser. No. 13/047,044, filed Mar. 14, 2011 (now U.S. Pat. No. 8,734,735), which is a divisional of application Ser. No. 12/696,506, filed Jan. 29, 2010 (abandoned) which is a divisional of application Ser. No. 11/010,773, filed Dec. 13, 2004 (now U.S. Pat. No. 7,722,810) which is a continuation of PCT Serial No. PCT/US02/30779 filed on Sep. 26, 2002 (expired), the disclosures of which are hereby fully incorporated by reference herein.

FIELD OF THE INVENTION

The present invention generally relates to apparatus and methods for handling and embedding tissue samples for biopsy analysis and, more particularly, for handling and embedding such samples in an automated manner.

BACKGROUND OF THE INVENTION

To accurately diagnose various tissue diseases and conditions, medical personnel must remove one or more samples of tissue from the body of a patient. This process of harvesting tissue from the body is known as a biopsy. Once the tissue sample or samples are removed and sent to a pathology laboratory, the tissue will go through a series of procedures performed by a histotechnician and, ultimately, a pathologist, in order to diagnose the tissue. The present invention generally relates to those procedures that are normally performed by the histotechnician to prepare the tissue sample or samples into slides that may be analyzed under a microscope by the pathologist.

Although the singular term "sample" is used throughout this specification, it should be understood that this term likewise encompasses plural "samples" as well. Once a tissue sample is removed from the body of a patient, it is typically placed into a specimen container containing a tissue fixative solution and then the container is transported to a pathology laboratory. The tissue will undergo a process known as "grossing-in" in the pathology lab during which a histotechnician will retrieve the tissue sample from the container, typically cut the tissue into appropriate sizes for tissue processing, place individual samples into the appropriate sized small plastic tissue cassettes, and assign tracking numbers to each cassette. These tracking numbers are then logged into a tracking system used in the laboratory. For the smallest tissue samples, which may only be scrapings, the cassette will have fine mesh openings on the sides and bottoms. In other situations involving very small tissue samples, the samples are placed into a bag that resembles a tea bag and prevents the smallest tissue samples from escaping. Larger tissue samples are placed into cassettes having somewhat larger slotted openings which are again smaller than the tissue sample inside the cassette.

The cassettes are then placed into a stainless steel perforated basket and run through a tissue processing machine, often overnight. This machine uses a combination of vacuum, heat, and chemicals to remove the interstitial fluids. Once the fluids have been removed from the tissue samples, the processing machine immerses the tissues samples in a bath of molten paraffin so that the interstices in the tissue are replaced with paraffin. The histotechnician then removes the basket from the machine and removes the individual tissue cassettes. At an embedding station, which has a molten paraffin reservoir and dispenser, the histotechnician will individually remove the tissue from each cassette. The histotechnician must carefully orient the tissue sample, based on tissue type, into a stainless steel base mold which is roughly the size of the tissue cassette and is partially filled with molten paraffin. The molten paraffin is then rapidly cooled on a refrigerated plate, which may be a thermal electric cooler (TEC), to partially solidify the paraffin thereby holding the tissue sample in the proper orientation. The cassette is then placed on top of the base mold and paraffin is poured through the opened top of the cassette into the base mold. The cassette changes its function at this point in the procedure from a tissue holding component to a fixation device for later use in taking shavings from the solidified wax or paraffin. The base mold is chilled until all of the molten paraffin has solidified and the histotechnician removes the stainless steel base mold from the block of embedded paraffin. The tissue sample is thus embedded within a rectangular block of paraffin with a plastic tissue cassette on the opposite side. As with the tissue processing machine, the embedding process is accomplished in a batch fashion during which an average histotechnician may embed approximately 40 to 60 cassettes per hour.

The blocks of hardened paraffin containing the embedded tissue samples are then ready to be sliced into extremely thin sections for placement on a microscope slide. This slicing operation is accomplished in a device known as a microtome. The histotechnician mounts the embedded tissue block in a chuck on the microtome which is sized to accept the side of the block that has the embedded plastic cassette. The histotechnician can then begin slicing the paraffin block which has the tissue sample embedded opposite to the plastic cassette surface. This yields a ribbon of individual slices of the tissue embedded in the paraffin. The action of the microtome causes the individual slices to stick together when done properly and, subsequently, these very thin ribbons of slices are floated into a water bath and a glass slide is carefully placed underneath the slice. The slice, with the thin sectioned tissue sample embedded therein, is then adhered to the top of the slide.

When the histotechnician has enough slides from the tissue sample, the slides are placed into an automatic staining machine. The staining machine goes through a series of infiltrating steps to stain the different tissue and cells of the slide different colors. This helps the pathologist identify different structures and makes it easier to find any abnormalities in the tissue. After the staining procedure is complete, the slides are cover slipped and prepared for the pathologist to place under a microscope to analyze.

Based on the summary of the procedure provided above, it will be appreciated that conventional tissue sample handling and processing is a very labor-intensive process involving several manual steps performed by a histotechnician. Thus, repetitive stress injuries such as carpal tunnel syndrome are prevalent. This is especially true with the tissue sample embedding process. These multiple manual operations and redundant handling increase the likelihood of human error and, moreover, require highly trained and skilled histotechnicians to ensure that the tissue samples ultimately adhered to the slides for analysis by the pathologist are in an optimum condition and orientation to make accurate diagnoses. The conventional methods for preparing tissue biopsy slides have been batch mode processes, as mentioned above, in which the histotechnician would move from process step to process step with a preselected number of cassettes based on the speed at which that histotechnician can operate.

One system and method has been developed to increase the productivity and reduce the occurrences of human error during the process of preparing tissue samples for biopsy analysis. In this regard, U.S. Pat. No. 5,817,032, the disclosure of which is hereby incorporated by reference herein, relates to a tissue trapping and supporting device, which may be a cassette, and which may be cut with a microtome. When a cassette is used, the tissue sample is immobilized within the cassette and subjected to the process for replacing tissue fluids with wax. Then, the tissue sample and the cassette are sliced at the same time for mounting on microscope slides. Because the tissue sample is never removed from the cassette from the time it is processed in the tissue processing machine to the time that it is cut with the microtome, a significant amount of time is saved and the chance for human error is significantly reduced due to the elimination of separate tissue handling steps. This patent also generally discusses an automated process which even further reduces the handling steps during the entire procedure.

In spite of the various improvements made in this field, there is an increasing need for additional reductions in handling and improvements in throughput production and consistent quality of embedded tissue samples.

SUMMARY OF THE INVENTION

The present invention generally relates to an automated machine for preparing tissue samples in respective microtome sectionable supports. The machine includes an input member configured to hold a plurality of the microtome sectionable supports prior to a tissue embedding operation. An output member is configured to hold a plurality of the microtome sectionable supports after the tissue embedding operation. A cooling unit is preferably configured to hold at least one of the microtome sectionable supports during the tissue embedding operation. More preferably, multiple thermal electric cooling (TEC) units are used for faster production, however, other cooling devices may be utilized without departing from the inventive principles. TECs are preferred because they can rapidly cycle between heating and cooling cycles. In accordance with the invention, initially cycling the TEC to heat the microtome sectionable support greatly assists with properly embedding the support. A motorized carrier assembly is mounted for movement and configured to hold at least one of the microtome sectionable supports. This carrier assembly moves the support from the input member to the cooling unit and, finally, to the output member. A dispensing device dispenses an embedding material onto the microtome sectionable support and at least one tissue sample carried by the microtome sectionable support during the embedding operation.

Preferably, the microtome sectionable support is received within a frame and is movable between a first position within the frame and a second position in which the embedded tissue sample is exposed for sectioning in a microtome. In this regard, the machine preferably also includes a staging device which operates to move the support from the first position to the second position. The staging device and the dispenser may be part of the same robot such that they move together between the plurality of cooling units. A sensor operates to detect an amount of the embedding material dispensed onto the microtome sectionable support. Another sensor detects the size and/or configuration of the cassette so that it may be placed into the properly configured base mold on one of the cooling units. The input member preferably comprises an elongate basket which is configured to hold and dispense a plurality of the microtome sectionable supports. The basket may be held within a heated receptacle and can include a dispensing opening. A positioning device urges the microtome sectionable supports toward the dispensing opening, such as through spring pressure and/or weights.

In the preferred embodiment, two different configurations of microtome sectionable supports may be processed in the machine, although it will be appreciated that the number of configurations processed by the machine can change. To this end, the machine further includes first and second molds thermally coupled with each cooling unit. The first mold is configured to receive a first microtome sectionable support and the second mold is configured to receive a second microtome sectionable support having a configuration different than the first microtome sectionable support. This different configuration, for example, may be a different size, a different shape, or any other characteristic difference between the first and second microtome sectionable supports. A cassette detection sensor detects the respective configurations of the first and second microtome sectionable supports and, as a result, the carrier assembly transports the microtome sectionable supports to the corresponding first or second molds.

These and other objects, advantages, and features of the invention will become more readily apparent to those of ordinary skill in the art upon review of the following detailed description taken in conjunction with the accompanying drawings.

BRIEF DESCRIPTION OF THE DRAWINGS

FIG. 21 is a flowchart illustrating a process executed by the control system of FIG. 17 to pick up a frame and cassette assembly from an input basket in the machine of FIG. 1.

FIG. 22 is a flowchart illustrating a process executed by the control system of FIG. 17 to test a frame and cassette assembly picked up from an input basket in the machine of FIG. 1.

FIG. 23 is a flowchart illustrating a process executed by the control system of FIG. 17 to load a frame and cassette assembly into a mold in the machine of FIG. 1.

DETAILED DESCRIPTION OF THE DRAWINGS

Figure 1:
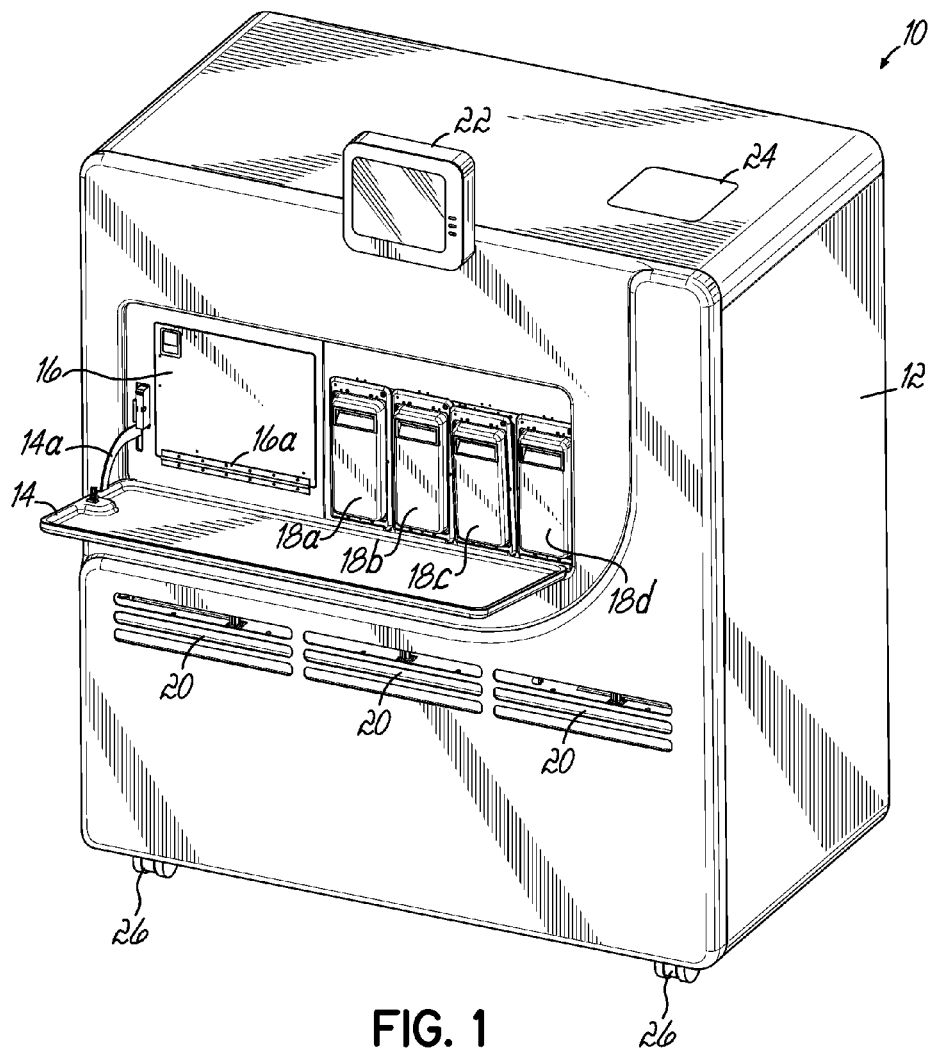
FIG. 1 is a perspective view of an automated machine constructed in accordance with the preferred embodiment of this invention for handling and embedding tissue samples.
Figure 2:
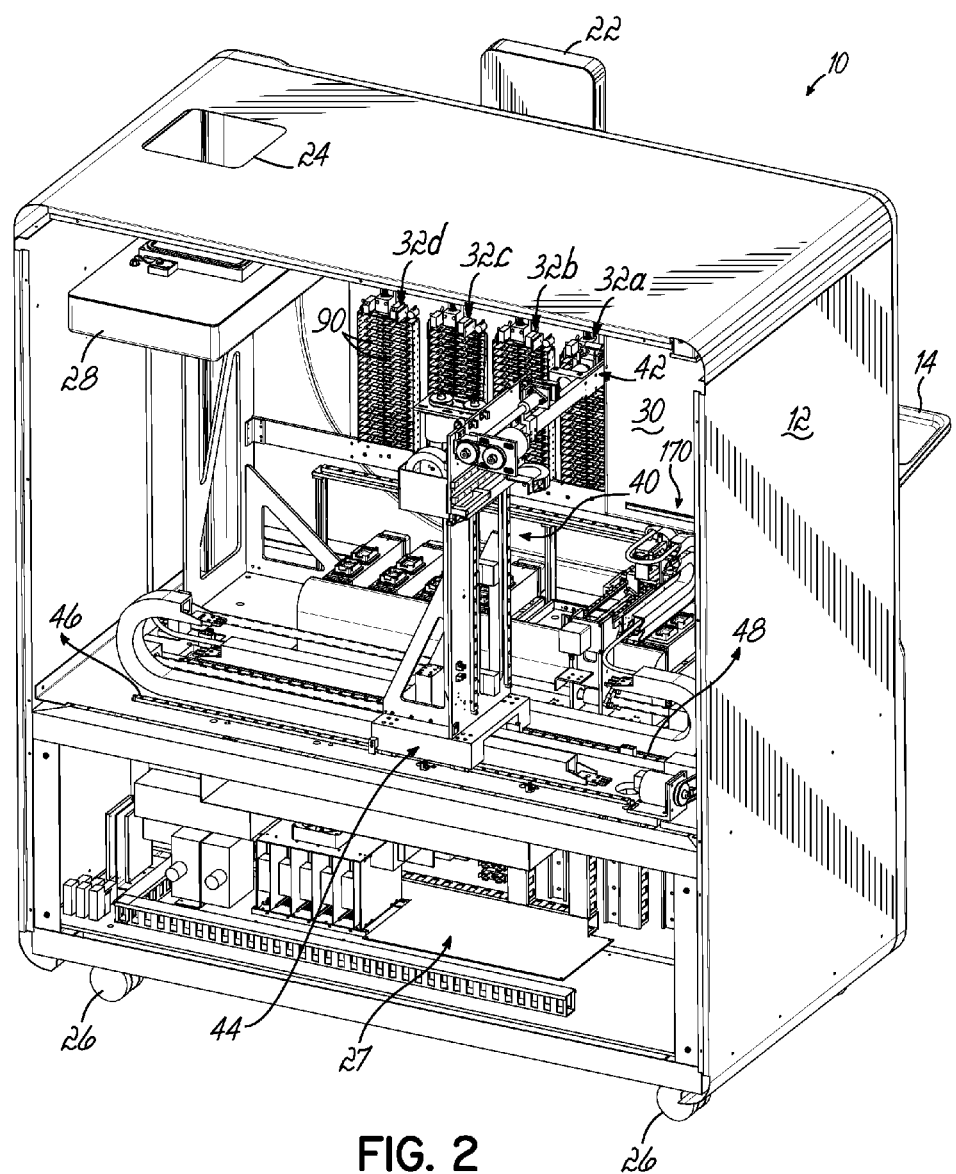
FIG. 2 is a rear perspective view showing the inside of the machine.

Referring generally to FIGS. 1 and 2, an automated machine 10 constructed in accordance with the invention includes a housing 12 having a main door 14 on its front side. When open as shown in FIG. 1, main door 14 exposes an input door 16 and four separate output trays 18a, 18b, 18c, 18d which are removable for purposes to be described below. Tray 18c is shown partially pivoted outwardly along its lower edge and ready to be lifted out of the machine 10. Doors 14 and 16 also pivot outwardly from their lower edges, however, doors 14 and 16 are attached to housing 12 by respective hinges 14a, 16a. The front side of housing 12 includes openings 20 which allow relatively cool room air to be drawn into thermal electric cooling devices as described below. Housing 12 includes a control panel 22 for operating the machine 10, a paraffin input opening 24 on its top side, and caster wheels 26 on its lower side. A lower inside portion 27 of housing 12 includes the various control components necessary to operate machine 10 as will be described below. As further shown in FIG. 2, paraffin input 24 leads to a container 28 for holding the liquid paraffin. Container 28 is heated to maintain the liquid paraffin at the proper temperature of about 60° C. As generally shown in FIG. 2, input door 16 leads to a cassette and frame assembly dispenser 30 while output trays 18a, 18b, 18c, 18d (FIG. 1) include individual cassette and frame assembly receivers 32a, 32b, 32c, 32d inside housing 12. Each receiver 32a-d has two vertical rows of spring-biased slots, each slot retaining a single cassette and frame assembly after the embedding operation is complete The machine 10 is loaded with cassette and frame assemblies each containing one or more tissue samples, in cassette and frame assembly dispenser 30. The cassette and frame assemblies or, more broadly speaking, the microtome sectionable supports, may take any suitable form. Preferably, these supports are generally of a form as described in U.S. Pat. No. 5,817,032, and further described below. The tissue samples are embedded in paraffin using the components and methods to be described below before being individually placed within the respective cassette and frame assembly receivers 32a, 32b, 32c, 32d.

Figure 3:
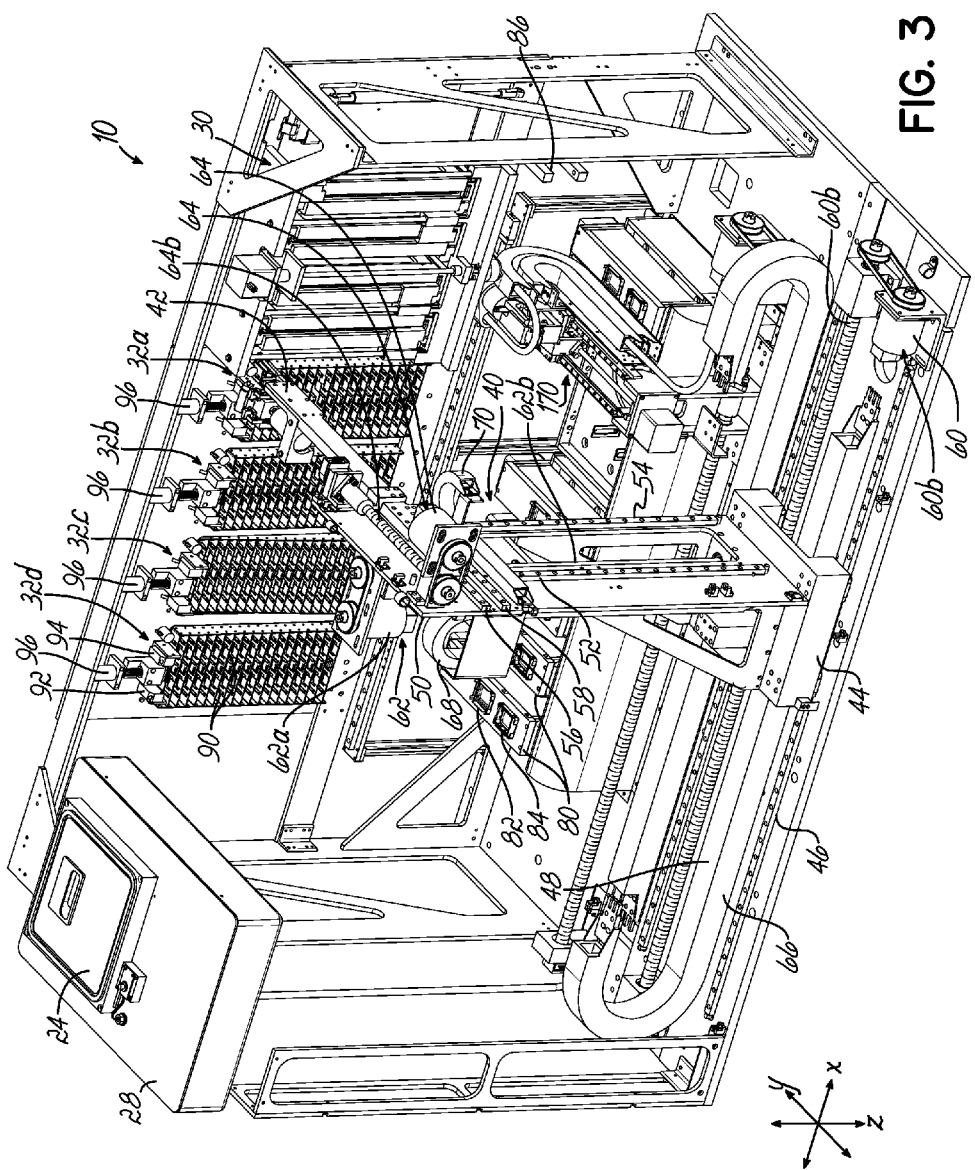
FIG. 3 is an enlarged rear perspective view with the outer panels of the machine housing removed and also the control component housing portion removed for clarity.

Referring now to FIG. 3, a pick and place robot 40 includes a pick and place head 42 which is movable along three axes. Specifically, a base 44 rides left and right on rails 46, 48 along a horizontal x-axis as viewed from the front of machine 10. Pick and place head 42 further rides on rails 56, 58 along a horizontal y-axis, that is, toward and away from the front of machine 10. A vertical support 50 carries pick and place head 42 and rides up and down on rails 52, 54 along a vertical z-axis. To achieve these respective movements, three separate motor and drive screw assemblies 60, 62 and 64 are provided. Motor 60a and drive screw 60b move base 44 along rails 46, 48. Motor 62a and drive screw 62b move pick and place head 42 vertically along rails 52, 54. Motor 64a and drive screw 64b move pick and place head 42 in opposite directions along rails 56, 58. Although belt driven screws are shown, it will be appreciated that direct drives or any other types of motive devices may be used instead. For all of the various electrical wiring that is necessary for the motors and control components, flexible conduits 66, 68, 70 are provided to facilitate the various movements of the pick and place robot 40.

Still referring to FIG. 3, pick and place robot 40 moves the cassette and frame assemblies from dispenser 30 to respective base mold modules or TEC units 80 and, more specifically, to one of two selectable base molds 82, 84 located on top of each TEC unit 80. Several TEC units 80 are removed for clarity. The use of TECs as integrated into units or modules 80 is advantageous because TECs may be quickly cycled between heating and cooling functions. As described below, each TEC unit 80 may be used to initially heat base mold 82 or base mold 84 such that liquid paraffin flows more completely into and throughout the cassette containing one or more tissue samples. This avoids air pockets in the paraffin after hardening which could lead to difficulties in subsequent steps taken by the histotechnician or pathologist. The number and type of cooling/heating units may be varied. Also, a greater or smaller number of base molds 82, 84 may be used, for example, to accommodate a range of configurations and/or sizes of cassette and frame assemblies to be processed in machine 10. The size and/or configuration of the cassette and frame assembly is detected with a suitable sensor 86 prior to transferring that cassette and frame assembly to a corresponding base mold 82 or 84. For example, a small biopsy cassette may have one or more holes detected by sensor 86, while a large cassette may not have such holes. Alternatively, machine readable indicia may be placed on the cassette and frame assemblies, such as a bar code, and then read by an appropriate device mounted in any suitable location. Thus, the cassette and frame assemblies may be identified and tracked within the machine. Thus, the machine control can identify which base mold 82 or 84 to place the cassette within.

Once the cooling process is complete (in a manner more fully described below) the pick and place robot 40 moves the cassette and frame assembly from a TEC unit 80 to respective slot receptacles 90 in one of the receivers 32a, 32b, 32c, 32d. Sensors 92, 94 are provided on each receiver 32a-d to indicate to the control system whether the associated receiver 32a-d holds any cassette and frame assemblies. Latch assemblies 96 are provided to retain trays 18a, 18b, 18c, 18d with their respective cassette and frame assembly receivers 32a-d on the front of housing 12. Preferably, these latch assemblies 96 are solenoid-operated to allow the control system of the machine 10 to monitor whether or not any particular tray 18a-d has been removed. If one has been removed, then machine 10 may stop operating or at least stop delivering embedded cassette and frame assemblies to the location of the removed tray.

Figure 4:
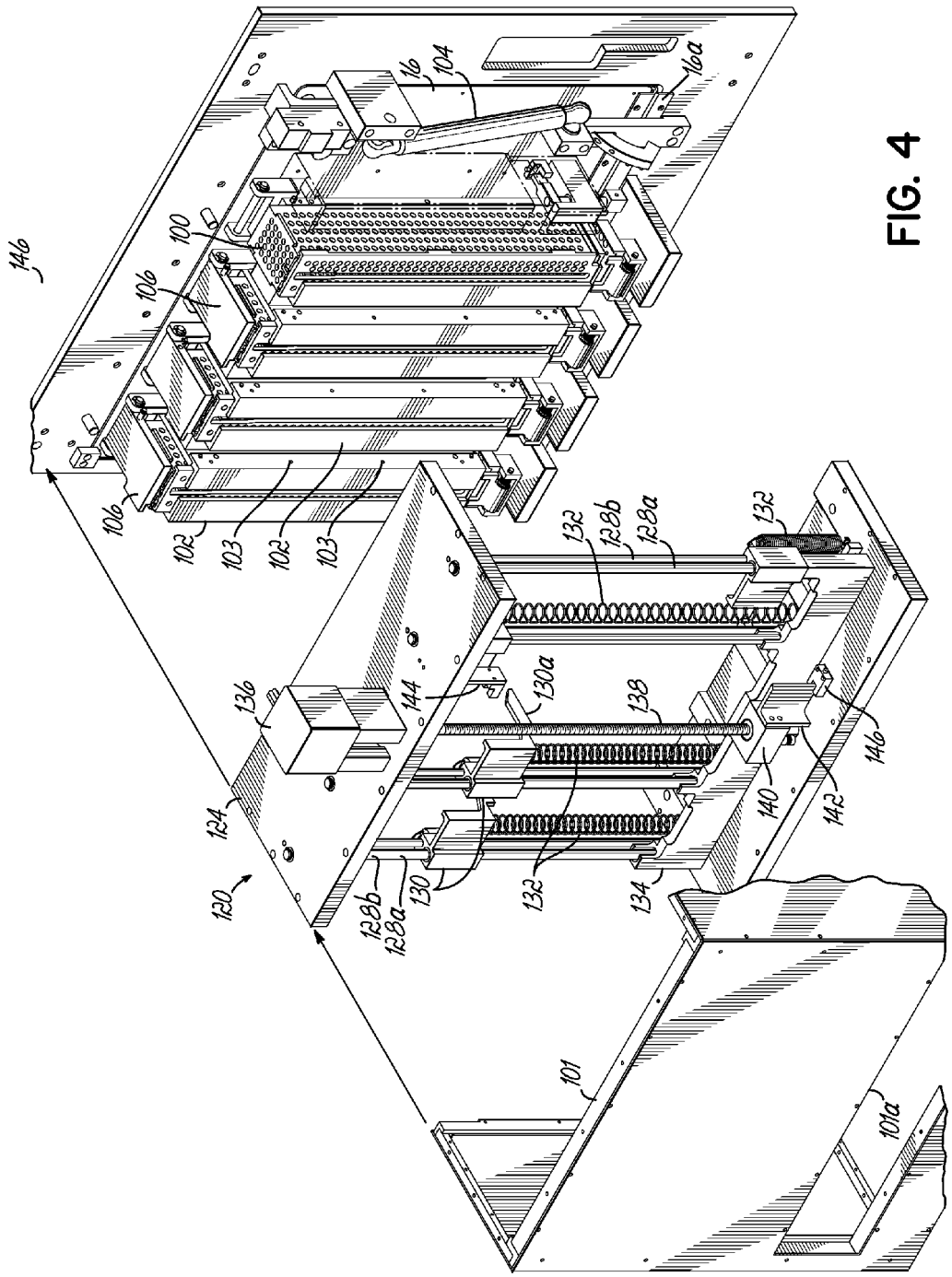
FIG. 4 is an exploded perspective view of the input door section of the machine.
Figure 4A:
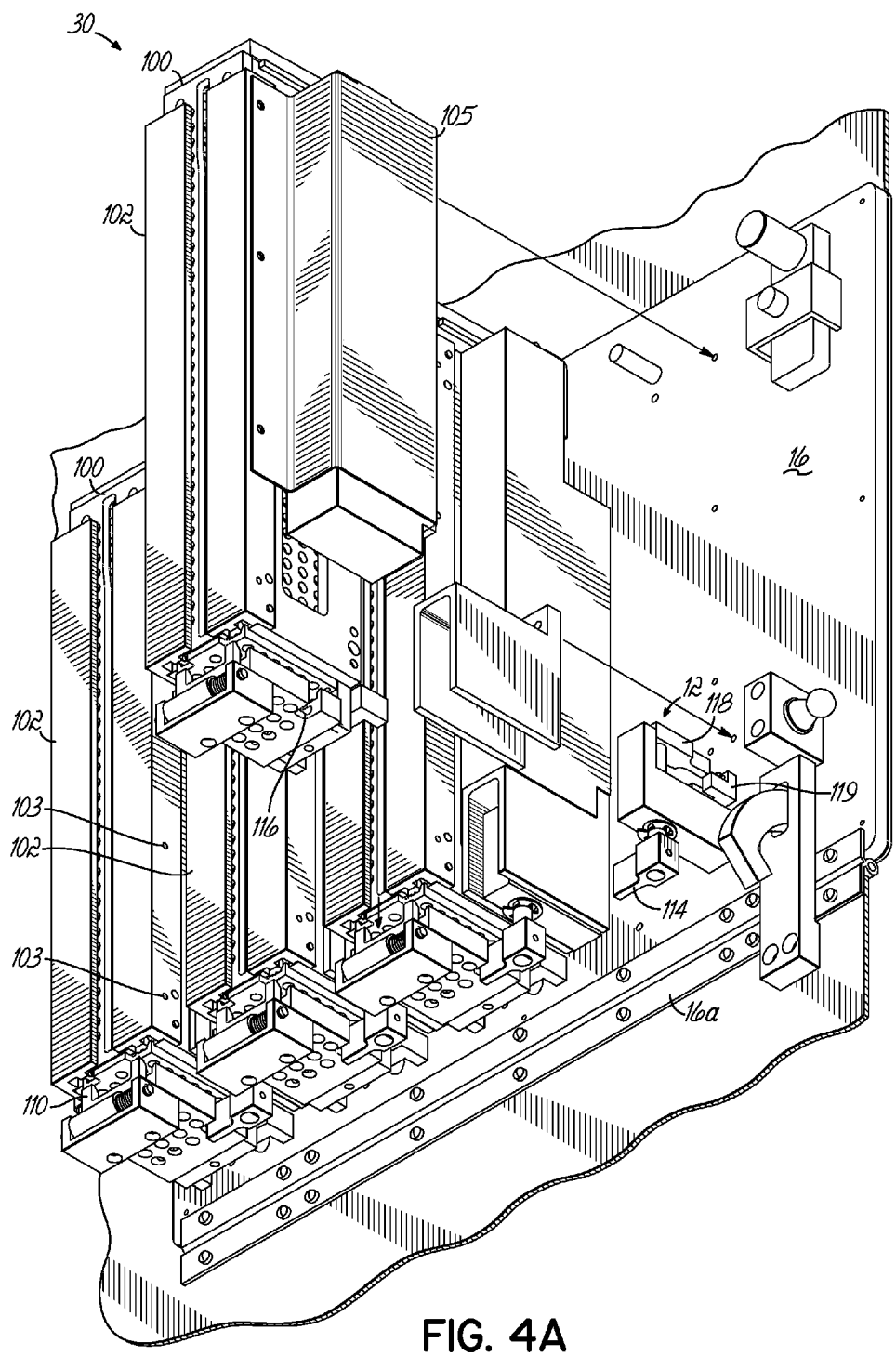
FIG. 4A is an exploded perspective view of the inside surface of the input door showing the cassette and frame assembly dispenser.
Figure 4B:
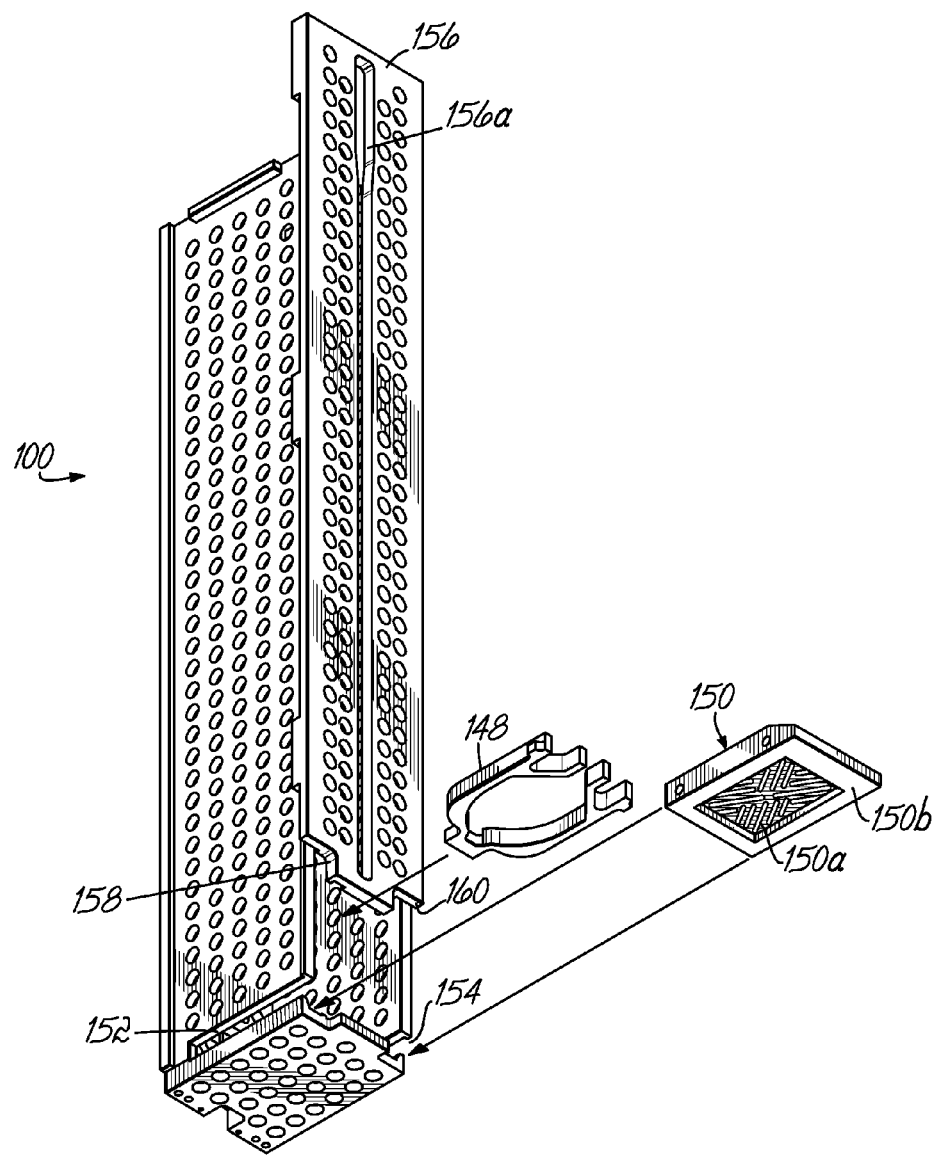
FIG. 4B is a perspective view of one of the input baskets showing one cassette and frame assembly as well as a retaining clip being inserted into the basket.

Turning to FIGS. 4, 4A and 4B, a plurality of, for example, four input baskets 100 are provided to hold the cassette and frame assemblies and their respective tissue samples for dispensing purposes. Access by pick and place head 42 is provided by an opening 101a in an interior cover 101. Each basket 100 is retained in a heated receptacle 102 on the inside surface of door 16. Preferably, receptacles 102 each include one or more cartridge style heaters 103 which maintain baskets 100 and the cassette and frame assemblies therein at an elevated temperature designed to keep any remnant paraffin remaining from the previous tissue processing procedure in a liquefied state until the start of the cooling process. That is, solidification of the paraffin is prevented so that the various components which need to move are able to without jamming. Suitable thermal insulation 105 may be provided between receptacles 102. Solidified or partially solidified paraffin on the baskets 100 and/or the cassette and frame assemblies therein may also tend to cause jamming of baskets 100 in receptacles 102 or jamming of the cassette and frame assemblies in baskets 100. Baskets 100 are preferably transferred by the operator, such as a histotechnician, directly into receptacles 102 from a tissue processing machine, however, this may instead be an automated transferring operation. Baskets 100 are perforated and constructed of a material suitably resistant to heat, chemicals, microwaves, or other environmental conditions present during tissue processing. A suitable material is Ultem®, available from General Electric Co. Baskets 100 may be accessed by opening door 16 via hinge mechanisms 16a, 104 (FIG. 4) and then opening a spring-loaded hinged closure 106 at the top of a basket receptacle 102. Each basket receptacle 102 further includes a lower, spring-loaded retaining member 110 which flips outwardly as a cassette and frame assembly is withdrawn from basket 100 and is then biased to the vertical position shown to retain the next successive cassette and frame assembly in position to be grasped by the pick and place head 42. A basket presence sensing assembly 112 is mounted to the inside surface of door 16 and is actuated when a basket 100 is fully inserted downwardly into receptacle 102 to thereby indicate to the control system that a basket 100 is present. Although such sensors may take many forms, in this case an actuation member 114 (FIG. 4A) is received in a slot 116 of basket 100 and is thereby moved downwardly such that an attached element 118 moves vertically into and is sensed by a presence sensor 119.

As further shown in FIG. 4, a positioning assembly 120 is used to ensure that all of the cassette and frame assemblies within each basket 100 are automatically and continuously moved to their lowermost positions ready for individual dispensing. Assembly 120 includes an upper plate 124 and a lower plate 126 coupled together by respective rods 128a, 128b. Rods 128a, 128b carry respective fingers 130 for vertical movement while preventing pivotal motion. It will be appreciated that although two rods 128a, 128b are shown coupled with each finger 130, other methods of preventing pivotal movement or otherwise ensuring the correct orientation of fingers 130 may be used instead. Fingers 130 are biased in a downward direction by preloaded springs 132. In addition, or alternatively, fingers 130 may carry weights, such as one to two pound weights (not shown), so that a constant downward force is applied to the cassette and frame assemblies 150 in baskets 100. This ensures that each successive cassette and frame assembly is moved into position for gripping and extraction as described below. A movable plate 134 is operated by a motor 136 and a screw 138 threaded into a nut 140. Plate 134 is moved upwardly from the position shown in FIG. 4 to move each of the fingers 130 to an uppermost home position thereby allowing removal of one or more of the baskets 100 from receptacles 102. Nut 140, which is rigidly attached to plate 134, carries a flange member 142 which actuates presence sensors 144, 146 at the respective end-of-travel positions to indicate to the control system when to stop motor 136 in each direction.

As illustrated in FIG. 4B, a retainer clip 148 is used to retain a stack of cassette and frame assemblies 150 (containing tissue samples, not shown) within basket 100. For illustration purposes, only one cassette and frame assembly 150 is shown. Assembly 150 includes an inner cassette 150a preferably constructed in accordance with the disclosure set forth in the above-incorporated U.S. Pat. No. 5,817,032 or in International Patent Application Serial No. PCT/US02/30775, the disclosure of which is fully incorporated herein by reference, and an outer frame 150b also preferably constructed in accordance with the referenced patent or patent application. As set forth in these prior disclosures, the tissue samples may be securely held between respective surfaces such that each tissue sample is immobilized in a specific orientation during the steps of processing the tissue samples, introducing liquid embedding material and hardening the liquid embedding material. In accordance with an embodiment of the present invention, basket 100 will be filled with, for example, 30-40 cassettes and frame assemblies 150, and retaining clip 148 will be used at the top of the stack of assemblies 150 to prevent any shifting of assemblies 150 within the basket 100 during handling. Basket 100 includes a pair of slots 152, 154 through which the lowermost cassette and frame assembly 150 is grasped by the pick and place head 42. Basket 100 further includes a removable cover 156 for allowing access to its interior. Cover 156 includes a slot 156a through which an extension 130a of one of the previously described fingers 130 (FIG. 4) will be inserted to bear against the top of the stack of cassette and frame assemblies 150 ensuring that a cassette and frame assembly 150 is always positioned adjacent slots 152, 154 for gripping purposes. The lower end of cover 156 also includes recesses 158, 160 to allow access by gripper fingers of the pick and place head 42 to be described below.

Figure 5:
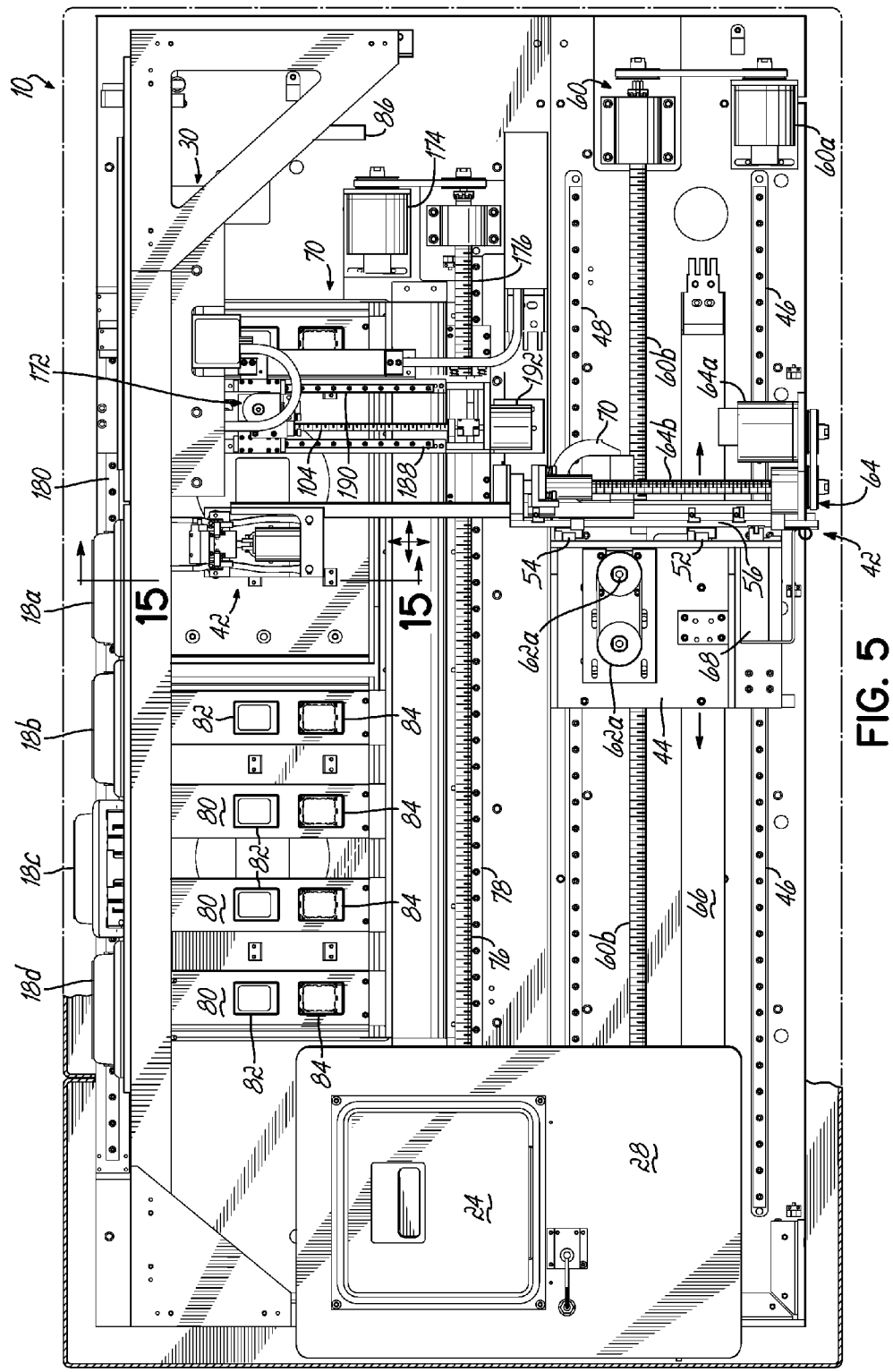
FIG. 5 is a top view of the inside of the machine.
Figure 6:
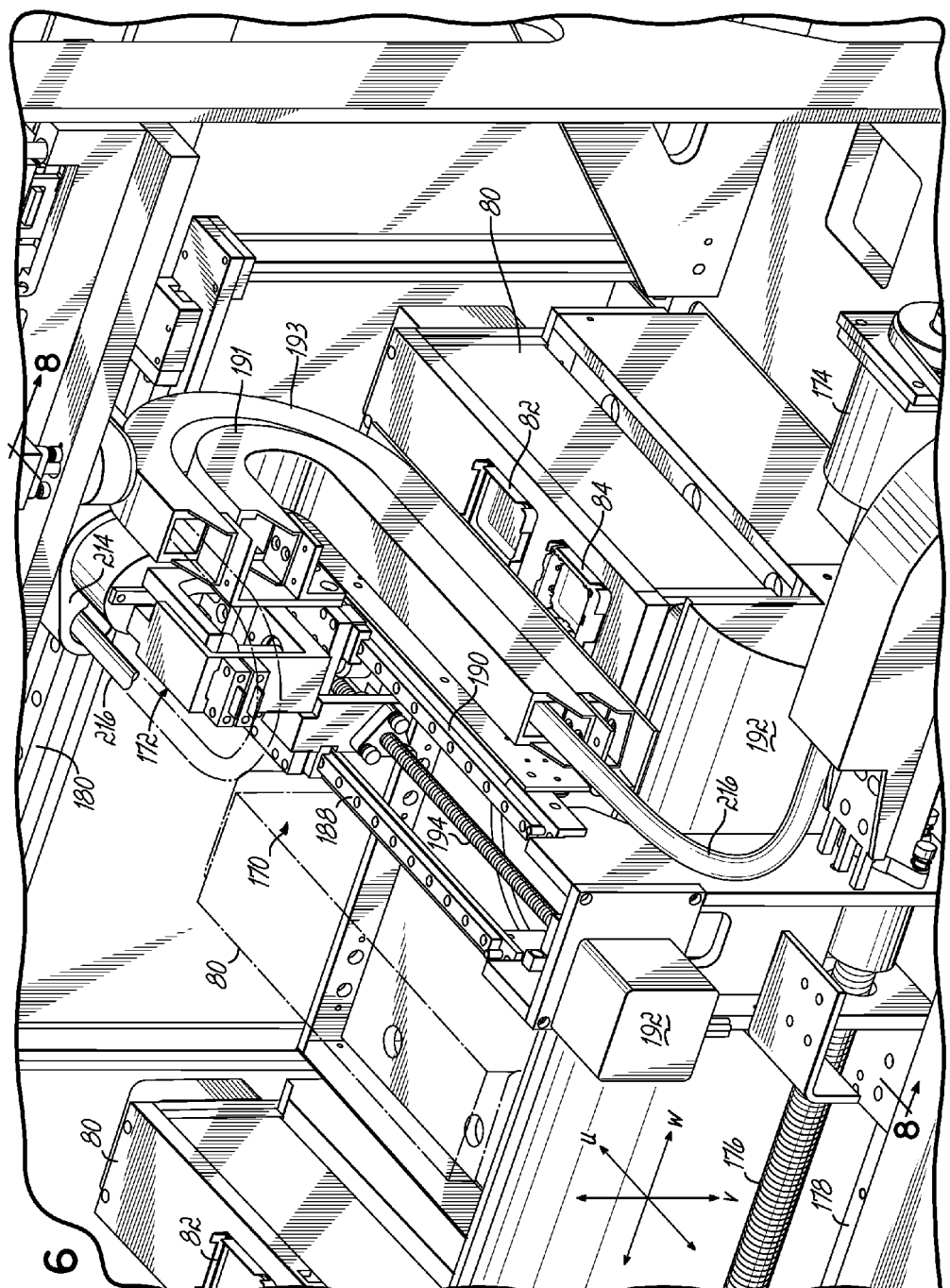
FIG. 6 is an enlarged perspective view of the staging robot in the machine.
Figure 7:
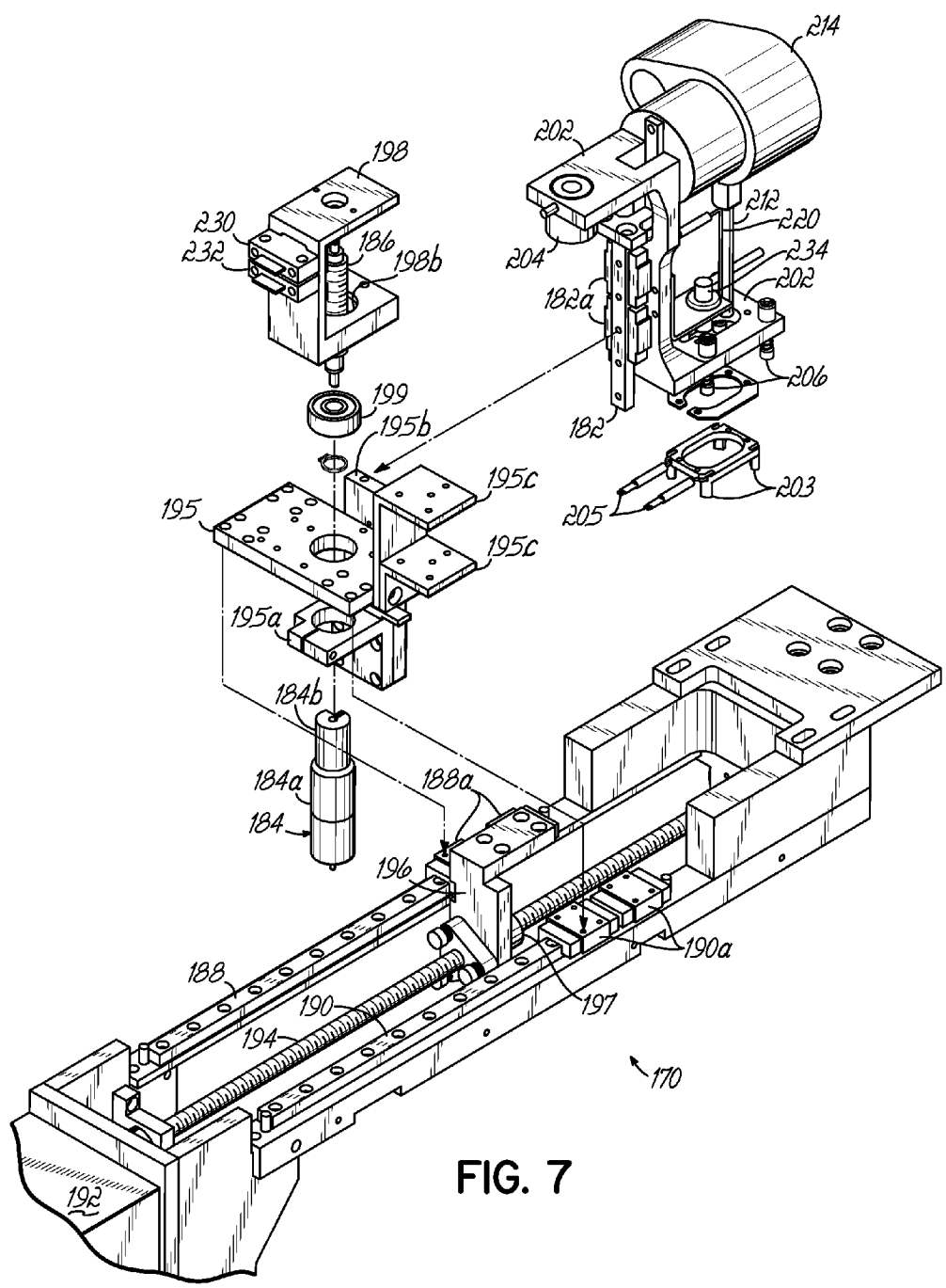
FIG. 7 is a perspective view of the staging robot with the stager/filler in exploded form.

Referring now to FIGS. 5-7, a staging robot 170 is also mounted for movement within housing 12 and includes a stager/filler 172 movable along three axes (u, v, w, see FIG. 6). Staging robot 170 is movable right and left (w-axis) via a motor 174 and drive screw 176 along rails 178, 180. Stager/filler 172 is further movable up and down (v-axis) along a rail 182 via a motor 184 and drive screw 186 (FIG. 7). Staging robot 170 is movable in opposite directions front to back (u-axis) along rails 188, 190 by a motor 192 and drive screw 194. Flexible conduits 191, 193 contain the electrical wiring and paraffin tubing as necessary during operation of staging robot 170. Once the pick and place robot 40 has placed a cassette and frame assembly 150 in one of the base molds 82 or 84, the staging robot 170 is moved along rails 178, 180 and 188, 190 to the correct position directly over the base mold 82 or 84 holding the cassette and frame assembly 150. Motor 184 and drive screw 186 are used to then vertically position stager/filler 172 as will be described below.

Figure 10A:
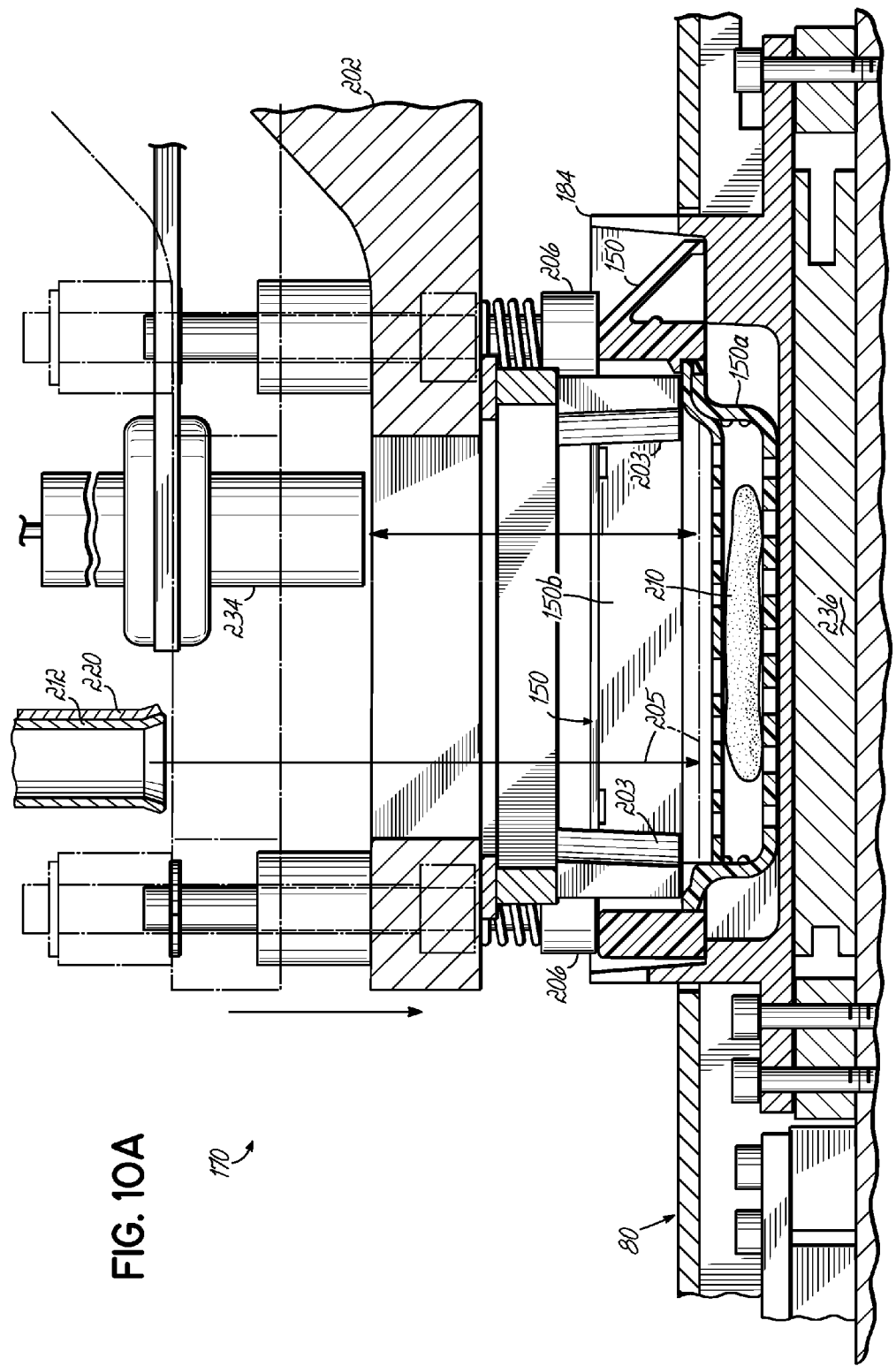
FIGS. 10A and 10B are enlarged cross sectional views similar to FIG. 9 and also progressively illustrating the staging operation.

Referring to FIGS. 7-10A and 10B, stager/filler 172 more specifically includes a support assembly 195 which is rigidly fastened to four linear bushings or bearing blocks 188a, 190a riding along rails 188, 190. Support assembly 195 is also rigidly fastened to a mounting member 196 which rides along screw 194 via a nut 197. Thus, motor 192 turns screw 194 through nut 197 and thereby moves support assembly 195 along rails 188, 190. A generally U-shaped support member 198 is a rigid part of assembly 195. As previously discussed, another motor 184 provides the motive force for vertical movement of stager/filler 172. Motor 184 includes a mounting portion 184a rigidly coupled to a mounting portion 195a of support assembly 195 and a rotatable portion 184b. A bearing 199 is held within a mounting hole 198b and supports screw 186 during rotation. Rotatable portion 184b of motor 184 is rigidly coupled to screw 186 such that screw 186 may be rotated within U-shaped support member 198. Stager/filler 172 further includes a vertical support member 202 carrying a nut 204 which engages screw 186. Vertical support member 202 is thereby moved along rail 182 via linear bushings 182a which are rigidly fastened to vertical support member 202. Rail 182 is rigidly fastened to a portion 195b of support assembly 195. Vertical support member 202 carries four fingers or pushers 203 which push cassette 150a through frame 150b and within base mold 82 to the position shown in FIGS. 9 and 10. Heaters 205 are also coupled to pushers 203 to maintain them at an elevated temperature (e.g., 60°-65° C.). Vertical movement of pushers 203 is accomplished by activating motor 184 and screw 186 such that vertical support member 202 carried by nut 204 moves downwardly along rail 182 and, as a result, moves pushers 203 downwardly against the top corner portions of cassette 150a. Simultaneously, vertical support member 202 moves four spring-loaded holding members 206 (only two shown) downwardly against the top corner portions of frame 150b to immobilize the frame 150b during the staging and paraffin filling process (FIG. 10A). After the staging process is complete, the bottom of the cassette 150a is exposed outwardly of the frame 150b and within the interior of the base mold 84.

Figure 10B:
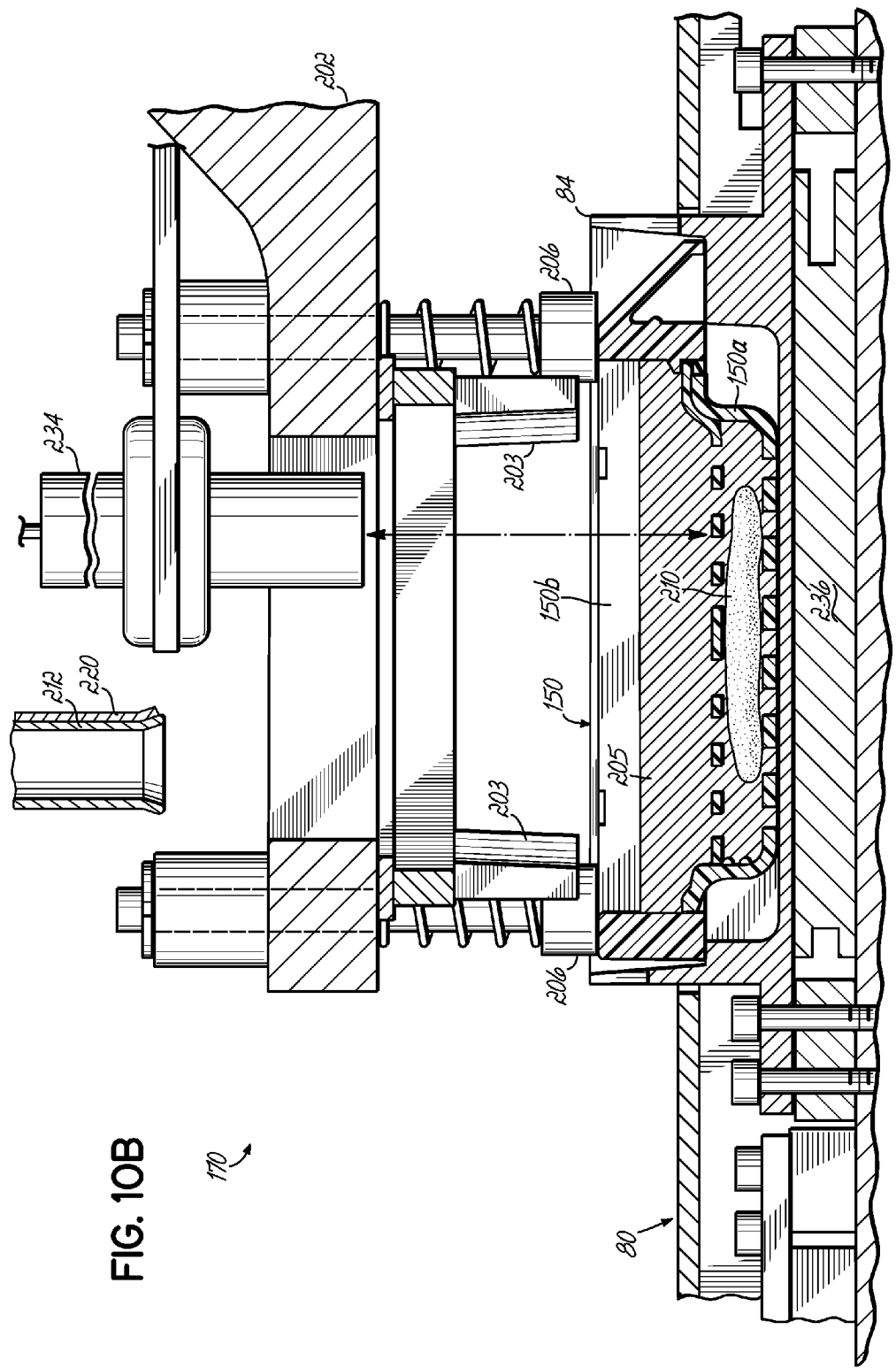

At this point, as shown in FIG. 10B, the fingers or pushers 203 are withdrawn upwardly by motor 184 to a position at which they will not contact any paraffin 205 while the spring-loaded holding members 206 still retain frame 150b against base mold 84 with some spring pressure. Liquid paraffin 205 is then dispensed into base mold 84 and throughout the cassette 150a to thereby embed the tissue sample 210. To this end, a dispensing tube 212 receives the paraffin from a suitable valve 214 and tubing 216 (FIG. 9) which is coupled to container 28 (FIGS. 2 and 3). As with all components which will be in close thermal contact with the paraffin, these components are preferably maintained at an elevated temperature of about 60°-65° C. Dispensing tube 212 is preferably heated by a cartridge heater 220 controlled by an RTD and thermal fuse assembly 224. Tubing 216 may be similarly heated, if necessary. The paraffin is preferably dispensed by gravity, although a pump may be used if necessary. Limit switches 230, 232 (FIG. 9) monitor the position of the vertical support member 202 at upper and lower limits. The intermediate position used during the filling procedure to raise pushers 203 above the paraffin level may be controlled by simply rotating the screw 186 a predetermined amount. An ultrasonic level sensor 234 (Model No. ML102 obtained from Cosense, Inc. of Hauppauge, Long Island, N.Y.) is mounted to the stager/filler 172 to sense when the level of liquid paraffin is correct, that is, preferably near the top of frame member 150b. At this point, the valve 214 is closed to stop dispensing paraffin from the dispensing tube 212. Level sensing is preferred because various amounts of paraffin will need to be added to each base mold depending on the amount of tissue in each cassette 150a. Thus, level sensing assures that there is no overflow or underfill of paraffin in the base mold 82 or 84.

After the filling operation is complete, the TEC unit 80 is activated to cool and solidify the liquid paraffin within the base mold 84 into a hardened block. This may take, for example, from one to three minutes. Since TECs are reversible between heating and cooling operations due to their use of a peltier-type of device, the TEC unit 80 may initially be used to heat the base mold 84 to allow better flow of liquid paraffin through the perforations of the cassette 150a. Better flow is achieved as a result of the lowered viscosity of the paraffin in the heated condition. This helps prevent air entrapment and assures that a preferred solid block of hardened paraffin is ultimately formed. As shown best in FIG. 8, each TEC unit 80 is constructed with two TECs which comprise conventional ceramic/metal plate assemblies and operate as peltier devices to provide surface cooling (or heating) through conduction with the bottoms of base molds 82, 84. Each TEC unit 80 includes an air flow passage 238 below TECs 236 with inlet and outlet fans 240, 242 for drawing air in through the openings 20 in the front of machine housing 12 (FIG. 1) and exhausting the air through a suitable exhaust conduit 244 leading to a lower portion of housing 12. This allows for heat to be appropriately transferred away from units 80 during the cooling cycle.

Figure 11A:
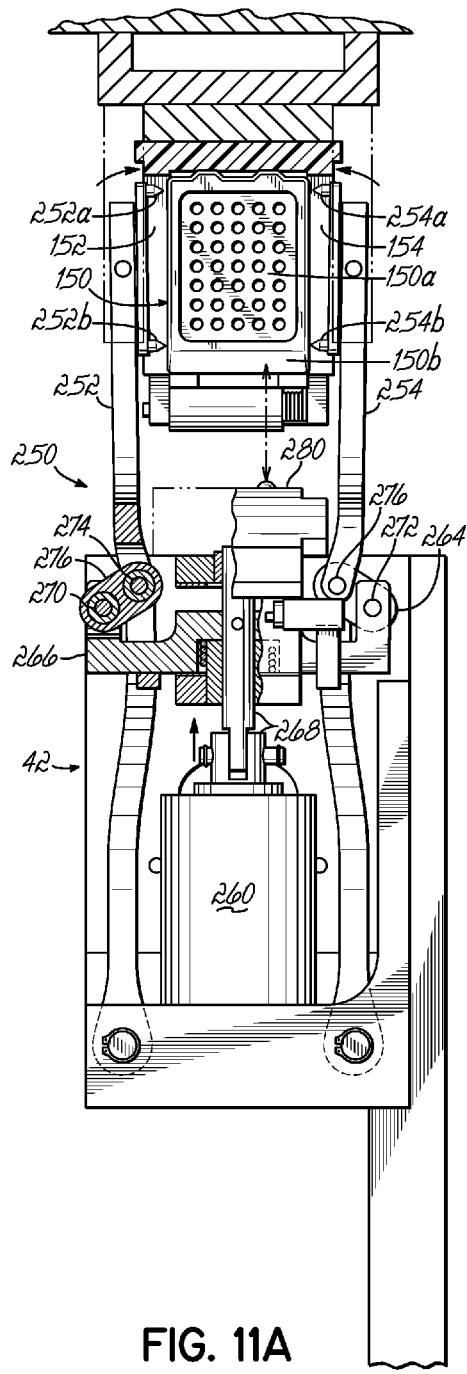
FIG. 11A is a cross sectional view taken along line 11A-11A of FIG. 12 and showing the gripper assembly just prior to gripping a cassette and frame assembly.
Figure 11B:
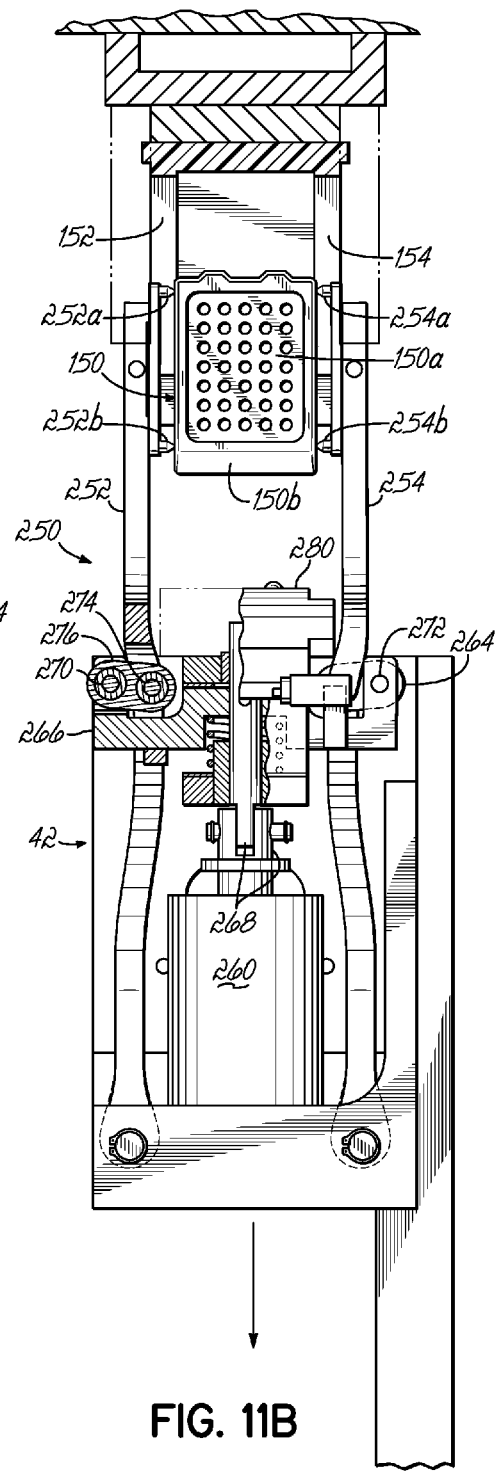
FIG. 11B is a partially cross sectioned top view similar to FIG. 11A, but illustrating the cassette and frame assembly gripped by the gripper fingers.

FIGS. 11A and 11B illustrate the specific gripping mechanism 250 used for grasping cassette and frame assemblies 150 on pick and place head 42. Specifically, a pair of opposed gripper fingers 252, 254 include respective projections 252a, 252b and 254a, 254b which register with indentations 256 (FIG. 14) in each frame 150b. An over-center type mechanism is used, operated by a solenoid 260, for moving fingers 252, 254 between an open or release position shown in FIG. 11A and a closed or gripping position shown in FIG. 11B. Linkages 262, 264 move between the position shown in FIG. 11A to the pivoted, over-center position shown in FIG. 11B. An actuating member 266 is connected to a reciprocating output 268 of solenoid 260 and pivotally connected to respective pivot points 270, 272 on each linkage 262, 264. Each linkage 262, 264 is further pivotally coupled to the gripper fingers 252, 254 at points 274, 276 such that reciprocating motion of actuating member 266 pivots the linkages 262, 264 and, at the same time, moves the gripping fingers 252, 254 inwardly or outwardly depending on whether the solenoid output 268 is moved outwardly or inwardly with respect to the solenoid 260. It will be appreciated that many other types of gripping devices may be used as alternatives to this type of device. In the preferred embodiment, an infrared presence sensor 280 is also carried on the gripping mechanism 250 to indicate whether a cassette and frame assembly 150 is present in the basket 100. If the presence sensor 280 does not detect a cassette and frame assembly 150, then the control system can direct the pick and place robot 40 to move the pick and place head 42, together with the gripper mechanism 250, to the next basket 100.

Figure 12:
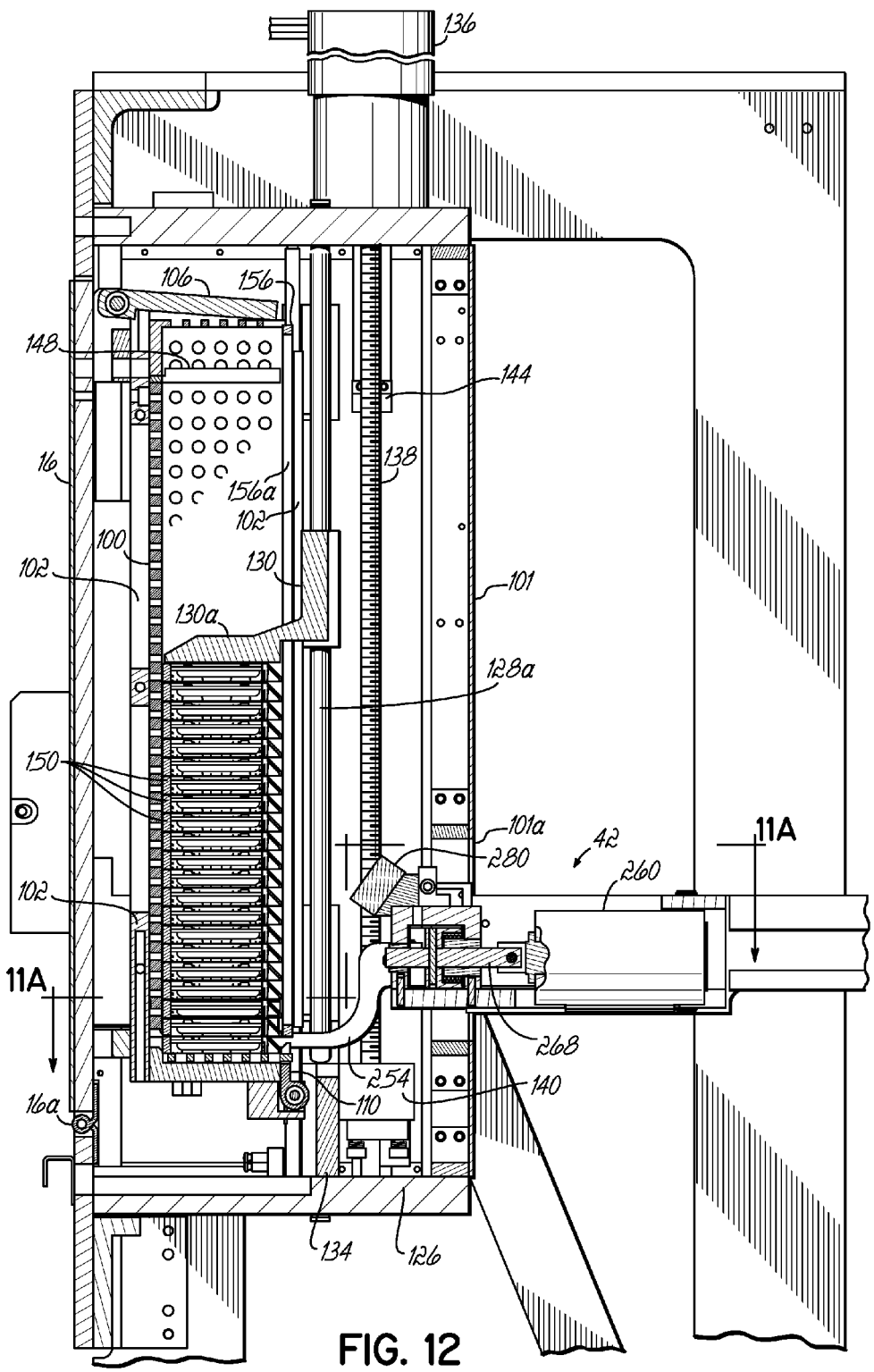
FIG. 12 is a cross sectional view taken along line 12-12 of FIG. 5 and illustrating the gripper assembly in the process of removing a cassette and frame assembly from an input basket.

The operation of machine 10 will now be described in connection with the previously described figures, as well as FIGS. 12-16. As shown in FIG. 4, receptacles 102 are loaded with respect with input baskets 100 each containing a number of cassette and frame assemblies 150. These input baskets 100 preferably are taken directly from a tissue processing machine (not shown) in which the tissue samples 210 (FIG. 10) contained in each cassette 150a have been processed in a known manner to replace the fluid in the tissue samples 210 with paraffin or another suitable material. In order to load the baskets 100 into the receptacles 102, the cassette positioning device 120 must be raised to its uppermost position allowing the input door 16 to be opened. When the input door 16 is then closed, the positioning device 120 lowers plate 134 thereby allowing fingers 130, 130a to lower under the force generated by springs 132 and/or weights (not shown). As shown in FIG. 12, pick and place robot 40 is moved such that pick and place head 42 and, more specifically, gripper fingers 252, 254 enter opening 101a and the dispensing slots 152, 154 of one of the baskets 100 (FIGS. 4, 4B). The gripper fingers 252, 254 grasp the lowermost cassette and frame assembly 150. Pick and place robot 40 then carries the gripped cassette and frame assembly 150 to sensor 86 (FIG. 3). Based on the reading from cassette sensor 86, the cassette and frame assembly 150 is carried to one of the base molds 82 or 84 which is empty and also corresponds to the configuration (e.g., size and/or shape) of the detected cassette and frame assembly 150. The pick and place head 42 drops the cassette and frame assembly 150 into the selected base mold 82 or 84 and then the pick and place robot 40 moves back to the input basket 100 to repeat the process during the initial start up. During normal operation, pick and place robot 40 will move to a cooled/hardened assembly 150 to one of the output slots 90 (FIG. 15), and then return to the input basket 100.

Figure 14:
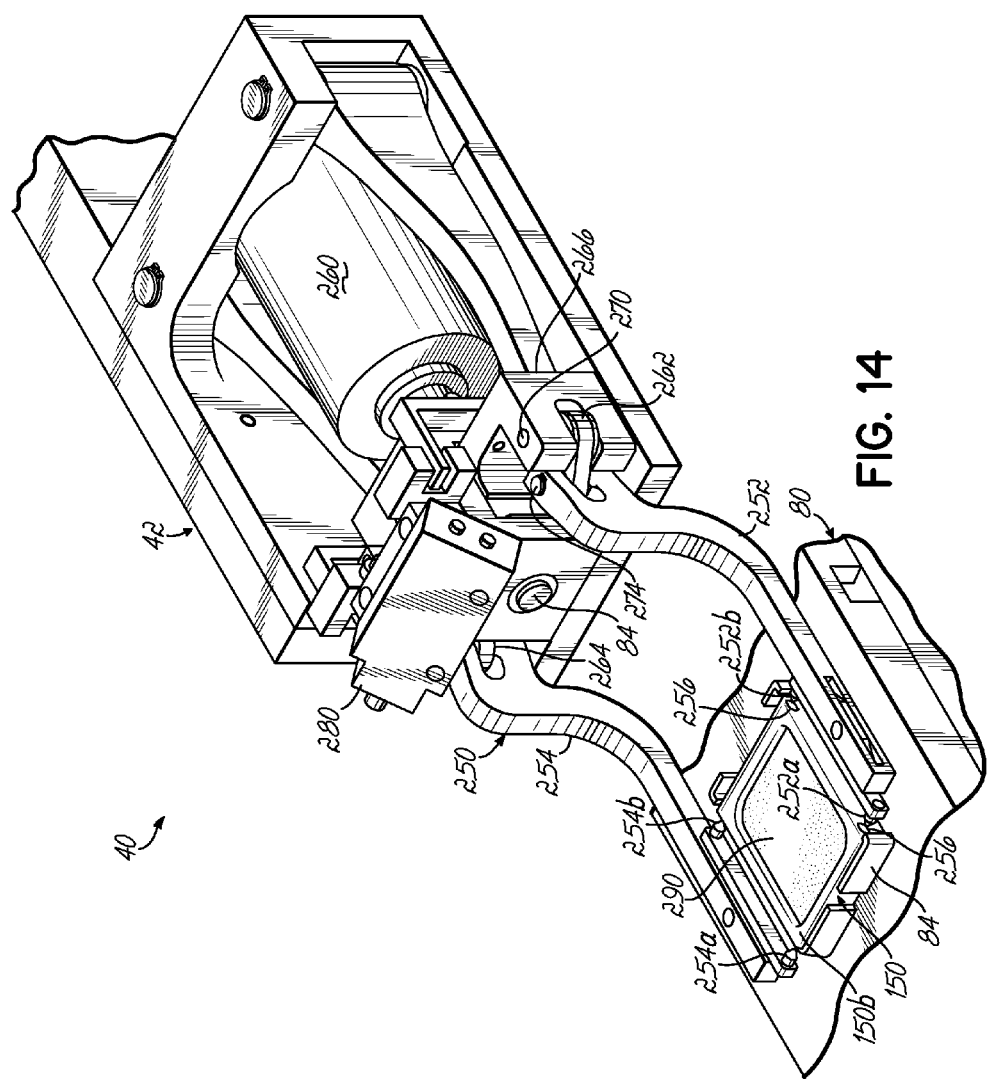
FIG. 14 is an enlarged perspective view illustrating a cassette and frame assembly being removed by the gripper assembly after the cooling operation is complete.
Figure 15:
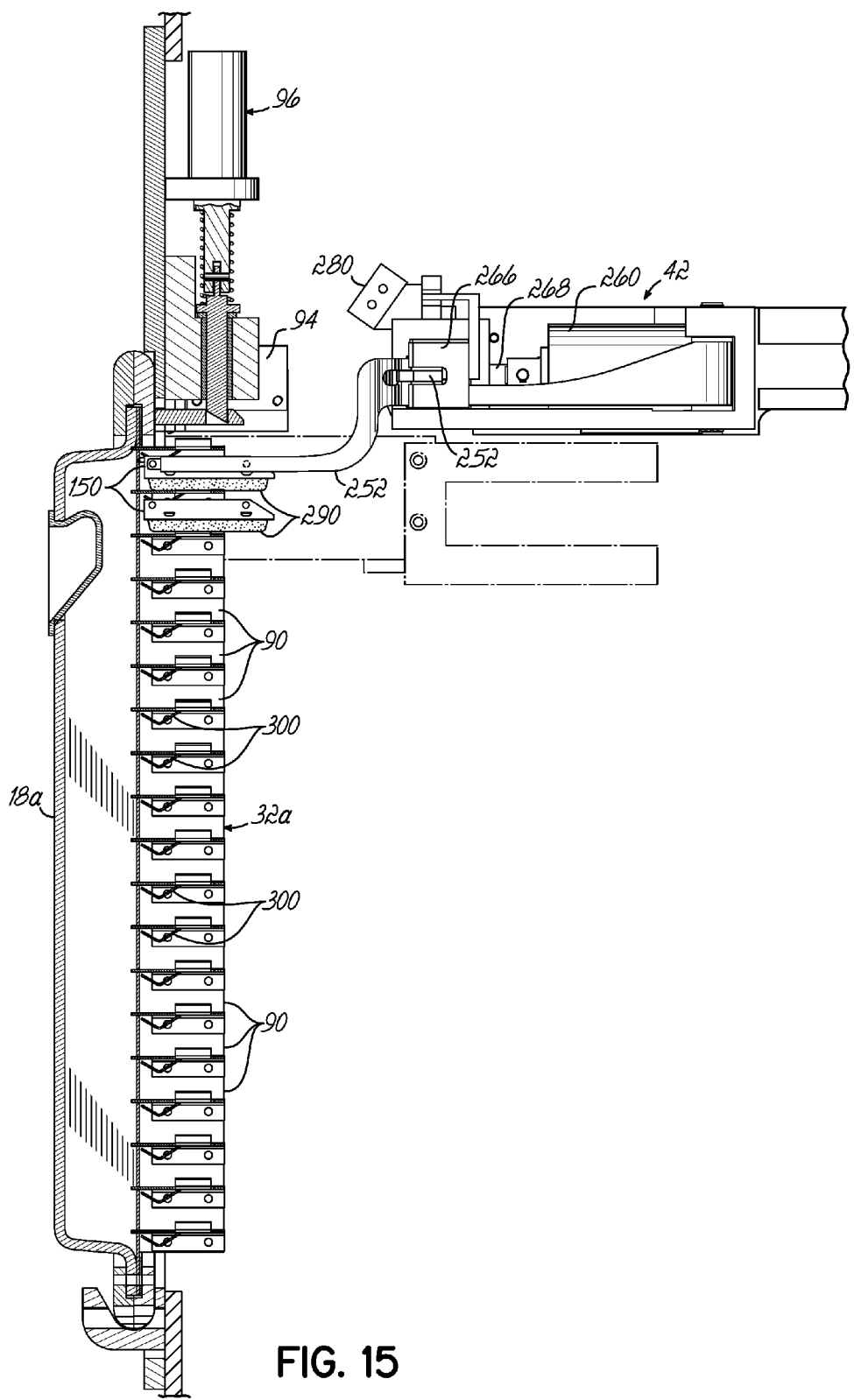
FIG. 15 is a cross sectional view of an output tray receiving cassette and frame assemblies which have completed the embedding process within the machine.
Figure 16:
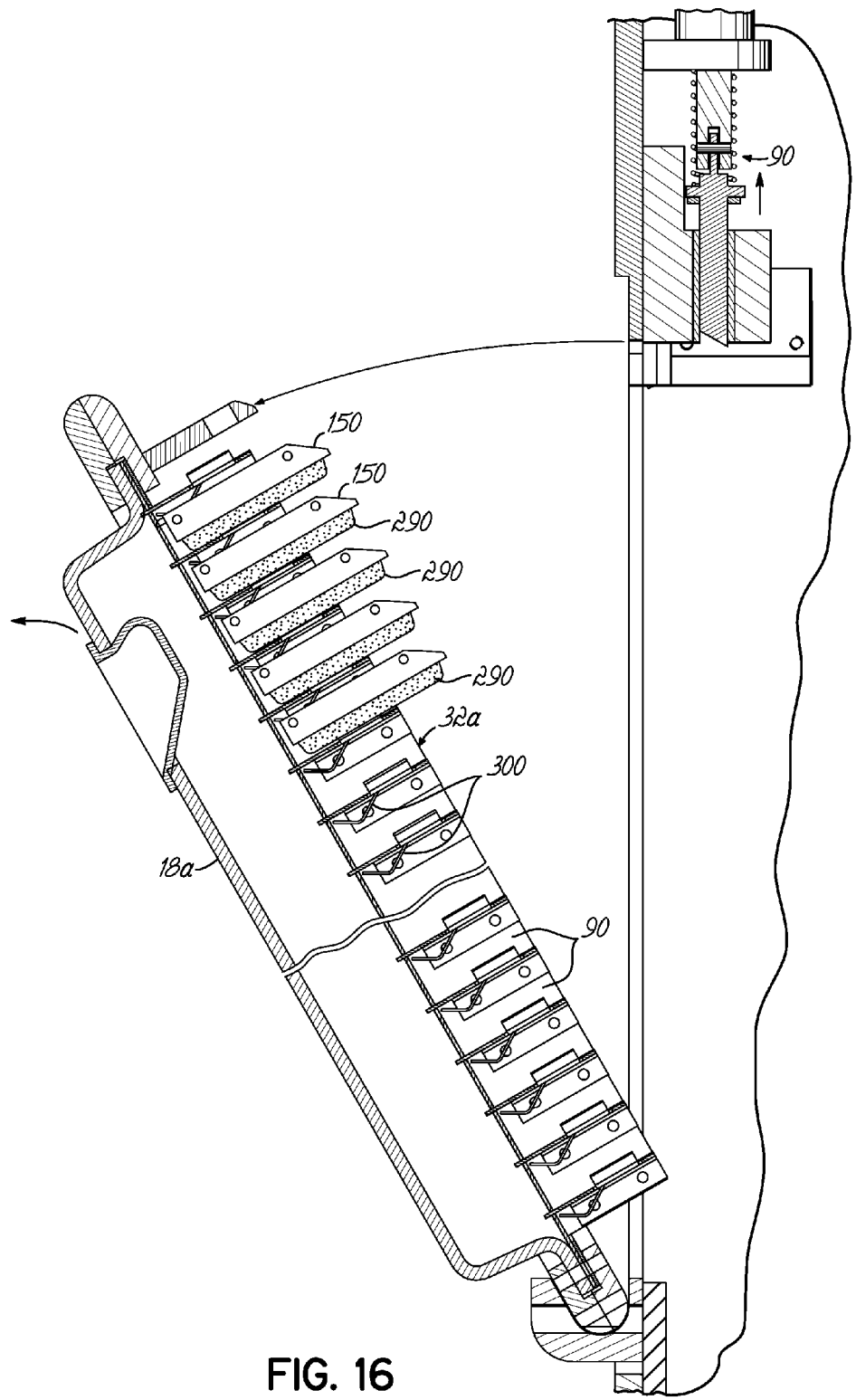
FIG. 16 is a cross sectional view similar to FIG. 15, but illustrating the removal of the output tray from the machine.

The staging robot 170 is then moved into position over the cassette and frame assembly 150 just loaded into the corresponding base mold 82, as shown in FIG. 6. As shown and described above in connection with FIGS. 8-10, the cassette 150a is staged (i.e., moved) into the base mold 82 and the base mold 82 is filled with liquid paraffin from dispensing tube 212. When the dispensing operation is complete, as detected by sensor 234, the staging robot 170 moves to the next position above another base mold 82 or 84 of a TEC unit 80 at which the pick and place robot 40 has loaded another cassette and frame assembly 150. The staging and filling operation is then repeated on the next successive cassette and frame assembly 150. As shown in FIG. 14, the pick and place head 42 is moved to the position of an embedded cassette and frame assembly 150 which has completed the cooling or hardening process on a TEC unit 80 and the cassette and frame assembly 150 is gripped using gripper fingers 252, 254. Pick and place robot 40 then moves the pick and place head 42 with the gripped cassette and frame assembly 150, now including a hardened block 290 of paraffin containing tissue sample 210, to one of the output trays 18a having slots 90 as shown in FIG. 15. The embedded cassette and frame assembly 150 is held within slot 90 by a spring loaded clip member 300 which frictionally engages the embedded cassette and frame assembly 150. At this point, the gripper fingers 252, 254 release the cassette and frame assembly 150. As shown in FIG. 16, output tray 18a may be removed by actuating solenoid 96, pivoting tray 18a outwardly, and lifting the tray 18a from the machine 11.

Figure 17:
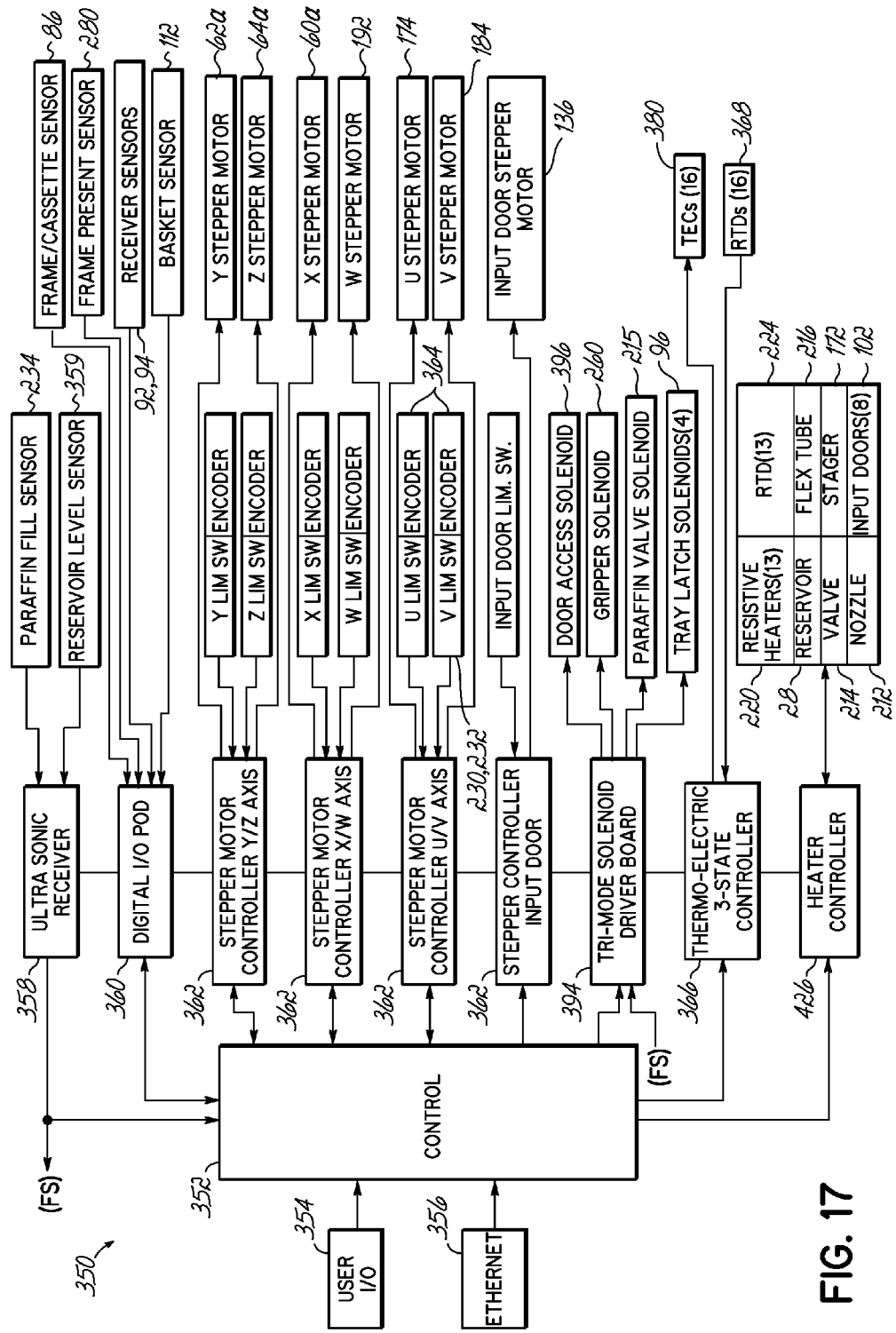
FIG. 17 is a schematic block diagram of a control system for the machine of FIG. 1.

The operation of the machine 10 is controlled by a system control 350 illustrated in FIG. 17. The system control 350 includes a control 352 that is connected to a user I/O 354, for example, a touch screen monitor. The control 352 is also, optionally, connected to an ethernet 356 to provide communication between the control 352 and another computer (not shown). The control 352 receives inputs from various sensors on the machine 10, for example, an ultrasonic receiver 358 that, in turn, receives inputs from the paraffin fill sensor 234 and reservoir level sensor 359. Other control inputs are connected to a digital I/O interface 360 that, in turn, is connected to various sensors, for example, the frame/cassette sensor 86, receiver sensors 92, 94, the frame present sensor 280 and the basket present sensor 112.

The control 352 provides command signals to stepper motor controllers 362 that, in turn, provide comparable command signals to the stepping motors 60a, 62a, 64a, and 192, 174, 184 and 136 in a known manner. The controllers 362 receive feedback signals from limit switches, for example, limit switches 230, 232 detecting the limits of travel along the v-axis. In addition, encoders 364 are coupled to respective stepper motors and provide respective feedback signals to respective stepper motor controllers 362, so that the commanded motion of each of the stepper motors can be confirmed. If a stepper motor controller 362 fails to detect a commanded motion of a respective stepper motor, the controller provides an error signal back to the control 352 for display on the monitor 354.

Figure 18:
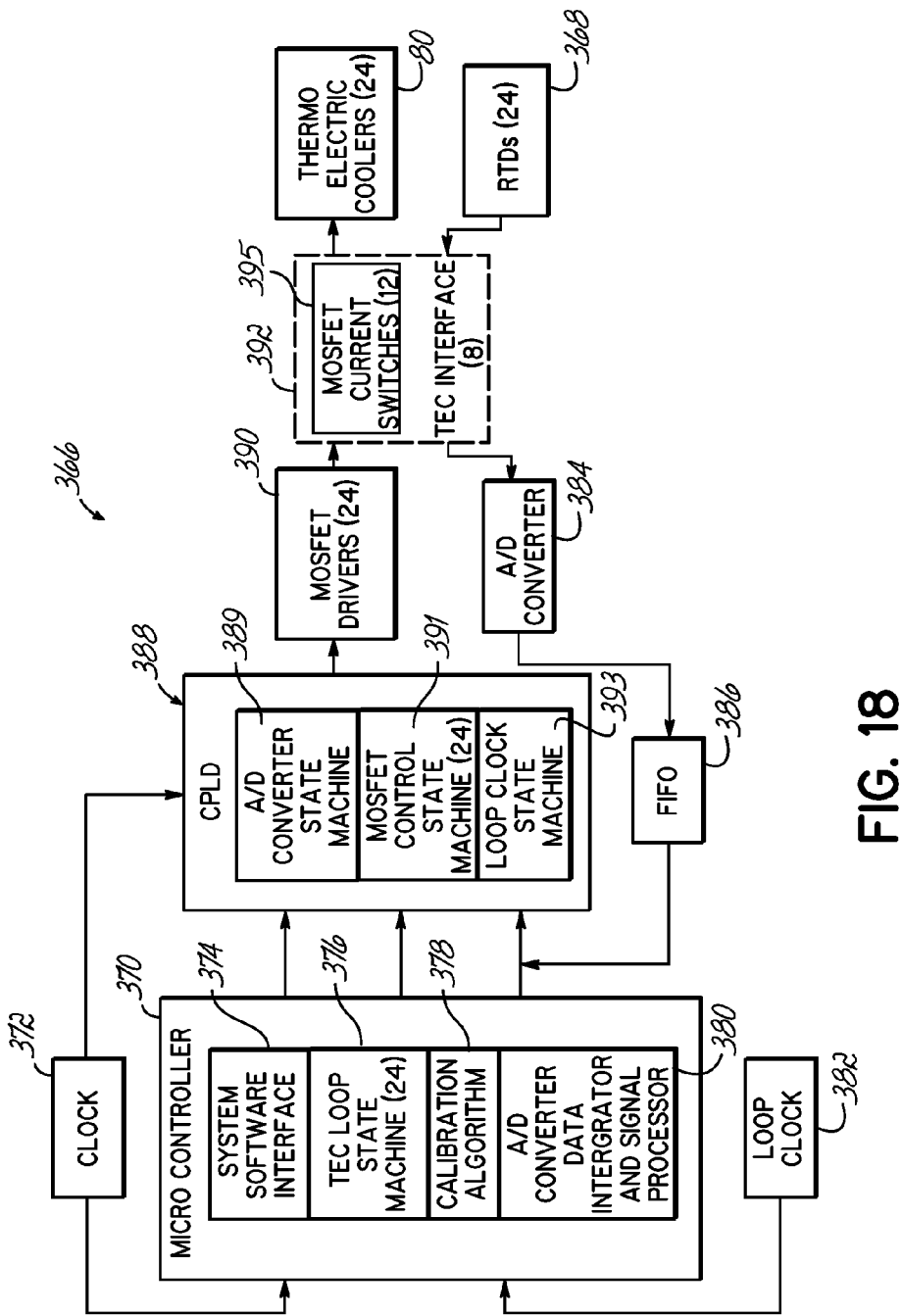
FIG. 18 is a schematic block diagram of a thermal electric 3 state controller used in the control system of FIG. 17.

The control 352 is further connected to a thermal electric 3-state controller 366 that controls the operation of each of the 16 TEC plates 236 associated with each of the 8 pairs of base molds 82, 84. Each TEC plate 236 has a corresponding RTD 368 that provides a temperature feedback signal to the controller 366 representing the temperature of its respective TEC plate 236. Referring to FIG. 18, the thermal electric 3-state controller 366 has a microcontroller 370 driven by a clock 372. It should be noted that although the machine has only 16 TEC plates 236, the controller 366 is built to accommodate 24 TEC plates 236. The microcontroller 370 includes software modules providing a system interface 374, a TEC loop state machine 376, a calibration algorithm 378 and an A/D converter and signal processor 380. The controller 370 controls all 16 TEC plates 236 and can be configured to control fewer or more TEC plates 236. In order to accommodate such a large number of devices, that is, 24 TEC plates 236 and 24 RTDs 368, a complex programmable logic device ("CPLD") 388 is used as an interface device between the microcontroller 370 and the TEC plates 236 and RTDs 368. A loop clock 382 provides successive time windows that are adjustable by the loop clock state machine 393 of the CPLD 388. During each time window, in response to a command from the microcontroller 370, the A/D converter state machine 389 within the CPLD 388 causes outputs from all of the RTDs to be multiplexed into the A/D converter 384. During each time window, RTD outputs are read by the microcontroller 370 as part of the microcontroller 370 regulating the operation of each of the TEC plates 236 in response to commands from the control 352 (FIG. 17). If the operating state of any of the TEC plates 236 is to be changed, a state of a MOSFET current switch 395 within the TEC interface 392 must be changed; and that new state is transferred to the MOSFET control state machine 391 of the CPLD 388. That new state is then supplied via a respective driver 390 to a respective current switch 395. Thus, the measured temperatures provided by respective RTDs 368 are maintained in close correspondence to the temperatures commanded by the control 352 (FIG. 17).

Figure 19:
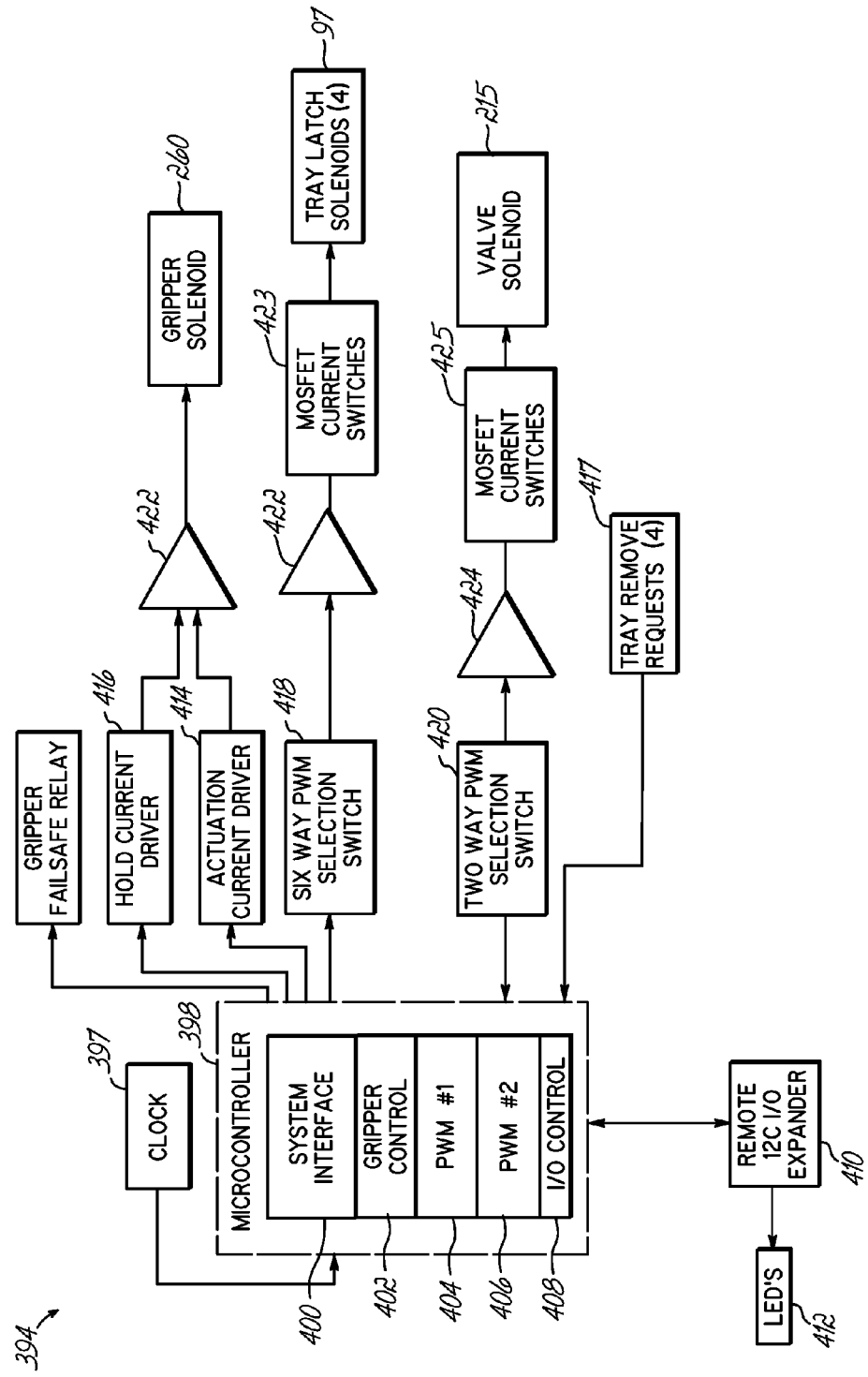
FIG. 19 is a schematic block diagram of a solenoid driver used in the control system of FIG. 17.

Referring back to FIG. 17, the control 352 provides command signals to a solenoid driver 394 that is operatively connected to the gripper solenoid 260, paraffin valve 214 and each of the four tray latch solenoids 97. Referring to FIG. 19, the solenoid driver has a clock 397 for a microcontroller 398 that includes software modules providing a system interface 400, a gripper control 402, pulse width modulators 404, 406 and an I/O control 408. The I/O control 408 provides output signals to the I/O interface 410 to drive solenoid status LEDs 412. In order to minimize heat within the machine 10, the solenoid driver 394 is designed to provide the minimum current necessary to operate the various solenoids on the machine 10. For example, the gripper control 402 operates the gripper solenoid 260 by first providing an actuation current to a driver 414 that, in turn, provides an output current to the solenoid 260 via amplifier 415. That actuation current is effective to rapidly actuate and change the state of the solenoid 260 and the gripper 250; and thereafter, the gripper control 402 provides a hold current to a driver 416 that, in turn, provides the minimum current necessary to hold the solenoid 260 in its current state.

A signal requesting one of the four tray latches be opened can be provided by input devices 417, for example, a push button on the machine or a button on the touchscreen of the user I/O 354 (FIG. 17). In response to that request, microcontroller 398 operates the pulse width modulator ("PWM") 404 to provide output signals to a PWM selection switch 418 that, in turn, provides actuation and hold currents via an amplifier 422 to an appropriate one of the MOSFET current switches 423. That MOSFET current switch 423 operates a respective one of the four tray latch solenoids 97, thereby releasing a latch or interlock so that a tray can be pivoted outward and removed. Similarly, in response to a command from the control 352, the microcontroller 398 operates the PWM 406 to provide actuation and hold currents signals to a valve solenoid 215 via two-way PWM switch selection 420, amplifier 424 and MOSFET current switches 425.

Referring back to FIG. 17, a heater controller 426 is responsive to commands from the control 352 to control the heaters 220 associated with the reservoir 28, valve 214, nozzle 212, feed tube 216 and the eight receptacles 102 on the input door 16. The heater controller 426 is operative to turn the heaters 220 on and off in order to maintain the temperature commanded by the control 352. The heaters are both resistive AC and DC heaters, and RTDs 124 are located close to respective ones of the heaters 220 to provide temperature feedback signals representing the temperatures of the respective devices being heated. In order for a heater control microcontroller to control such a large number of heaters and RTDs, a loop state machine and CPLD can be used in a manner similar to that described with respect to the TEC controller of FIG. 18. Zero crossing TRIAC current switches can be used in a known manner to control the operation of the DC and AC heaters, respectively.

In use, in order to load the baskets 100 into the receptacles 102, an operator uses the touchscreen monitor 354 to command the cassette positioning device 120 to raise to its uppermost position, thereby allowing the input door 16 to be opened. After the baskets 100 have been placed within the machine 10, the input door 16 is then closed. The operator again utilizes the touchscreen monitor to command the positioning device 120 to lower plate 134, thereby allowing fingers 130, 130*a* to lower under the force generated by springs 132 and/or weights (not shown). As will be appreciated, the process of moving the cassette positioning device 120 and opening and closing the input door 16 can be fully automated. In addition, the operator loads output trays 18 into the machine 10.

The processing of frames and cassette assemblies 150 is conducted in three operating modes. In a first load molds mode, frame and cassette assemblies are successively transferred from baskets 100 to one of the molds 82, 84 (FIG. 3) of each of the eight pairs of molds; and the filling and cooling cycles are initiated. After the eight molds 82 or 84 have been loaded, filled and are cooling, the control 352 initiates a continuous processing mode, in which cooled frame and mold assemblies 150 are successively moved from the molds 82 or 84 to output trays 18. The emptied molds are immediately reloaded with another frame and cassette assembly 150 from a basket 100, and the continuous mode continues until all of the assemblies 150 have been unloaded from a basket 100. Thereafter, the control 352 initiates an unload molds mode in which the remaining cooled frame and cassette assemblies are moved from the molds 82, 84 to the trays 18.

Figure 20:
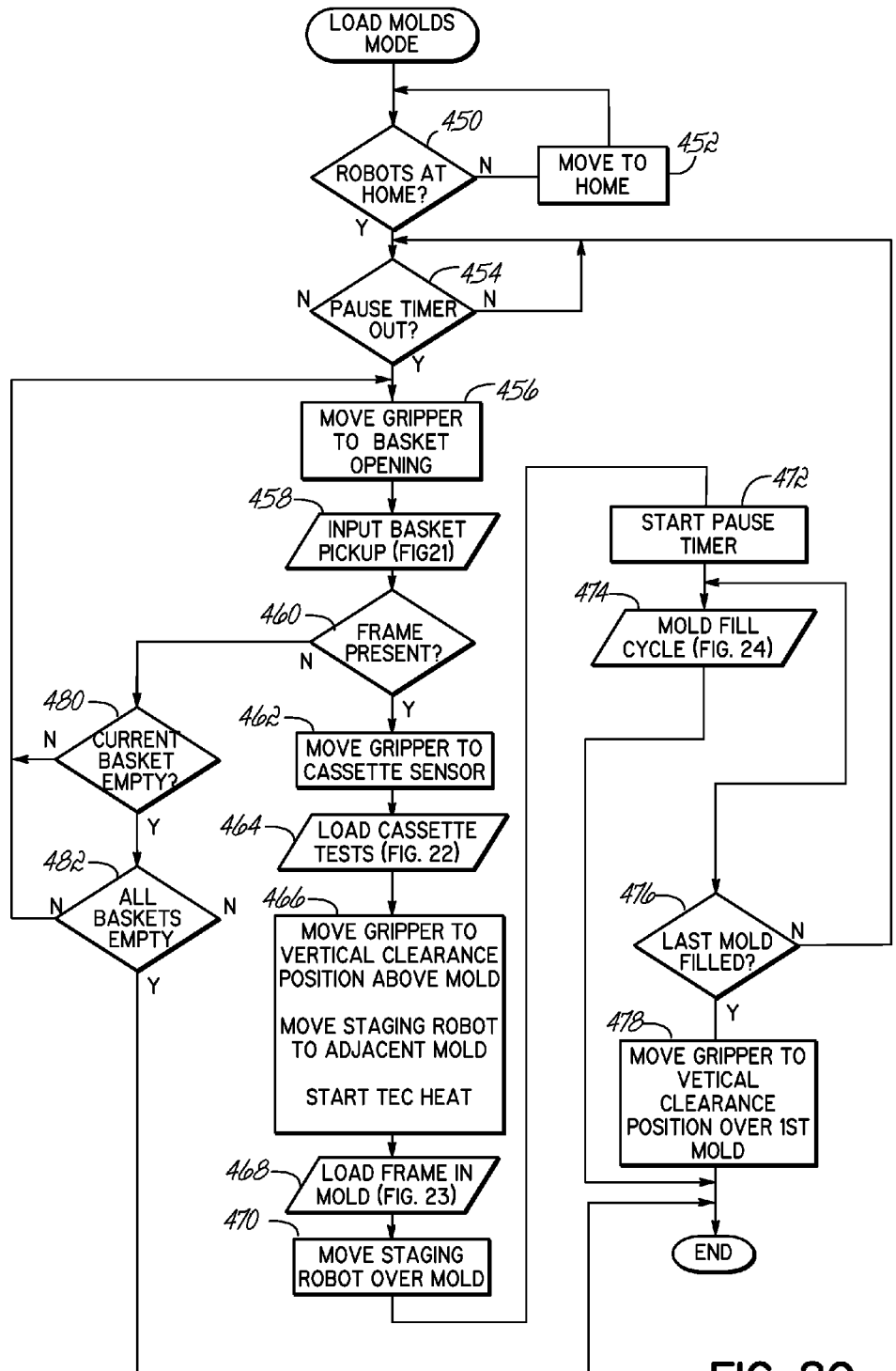
FIG. 20 is a flowchart illustrating a process executed by the control system of FIG. 17 to continuously load frame and cassette assemblies from baskets into molds in the machine of FIG. 1.

To initiate processing, the operator again utilizes the touchscreen monitor 354 to command a cycle start. In response to that command, the control 352 executes a load molds cycle as shown in FIG. 20. The control 352 first, at 450, determines whether transport robot 40 and staging robot 170 are at their home positions by monitoring the states of limit switches 364. The home position of the transport robot 40 is defined at the x-axis travel limit closest to the first mold to be filled, the upper z-axis limit and the forward, relative to the machine 10, y-axis limit. The home position of the staging robot 170 is defined at the x-axis travel limit closest to the last mold to be filled, the upper z-axis limit and the forward, relative to the machine 10, y-axis limit. If either of the robots is not at its home position, the control 352 provides, at 452, command signals to the stepper motor controllers 362 to operate the stepping motors and move the robots to their home position. After determining, at 454, that a pause timer is not operating, the control 352 commands the controllers 362 to move, at 456, the gripper 250 to a position outside but immediately adjacent to an opening 101 (FIG. 4) adjacent a basket 100. Thereafter, the control 352 executes, at 458, an input basket pickup subroutine illustrated in more detail in FIG. 21.

In executing this subroutine, the control 352 first, at 602, commands the solenoid driver 394 to actuate the gripper solenoid 260 and open the gripper fingers 252 (FIG. 11A). Thereafter, the control 352 commands, at 604, the appropriate controller 362 to operate the stepper motor 64*a* and move the gripper fingers 252 through the opening 101*a* (FIG. 12) and into the basket 100. The control 352 then commands, at 606, the gripper fingers 252 to close (FIG. 11B); and, at 608, the stepping motor 64*a* to reverse its motion and return the gripper fingers 252 to their original position immediately adjacent the opening 101*a*. Thereafter, the control 352 reads, at 610, the state of the frame sensor 280 located on the gripper 250. The operation of the load molds cycle of FIG. 20 continues by the control 352 determining, at 460, whether a frame 150*b* is present in the gripper 250.

If so, the control 352 commands, at 462, the stepping motors to move the gripper 250 to the cassette sensor 86 (FIG. 3). At 464, the control 352 executes a load cassette test subroutine illustrated in more detail in FIG. 22. Several tests are performed utilizing the sensor 86 to determine, at 620, that a frame and cassette assembly 150 is properly oriented in the gripper 250. For example, it is possible that the assembly 150 may have inadvertently been loaded upside down or inadvertently rotated front to back. Next, the control determines, at 622, that a cassette 150*a* (FIG. 4B) is located in the frame 150*b*. The sensor 280 on the gripper 250 is only capable of detecting the presence of a frame portion 150*b* of the frame and cassette assembly 150; and therefore, it is important to determine that the frame 150*b* does support a cassette 150*a*. Further, the machine 10 is capable of processing cassettes of two different sizes; and therefore, at 624, the control 352 manipulates the gripper 250 such that the sensor 86 can be used to detect which size cassette is currently in the gripper.

When a size is detected, an appropriate flag is set at 626, 628. If an error is detected in any of the tests, the control 352 provides, at 630, a display of the error on the monitor 354; and it ends its cycle of operation until the error has been corrected.

Returning to the load molds cycle of FIG. 20, after the load cassette tests have been successfully completed, the control 352, at 466, commands the gripper 250 to be moved to a vertical clearance position above one of the mold pairs that is empty and corresponds to the cassette size that was detected, for example, a first one of the molds 82 (FIG. 3). In addition, the control 352 commands the staging robot 170 to move from its home position to the right to a position immediately adjacent the mold 82. Further, the control 352 provides an output signal commanding the thermal electric controller 366 to turn on the TEC plate 236 associated with the mold 82. The thermal electric controller 366 utilizes the temperature feedback signal from the RTD 368 to operate the TEC plate 236 such that the mold 82 is heated to a desired temperature.

Figure 13:
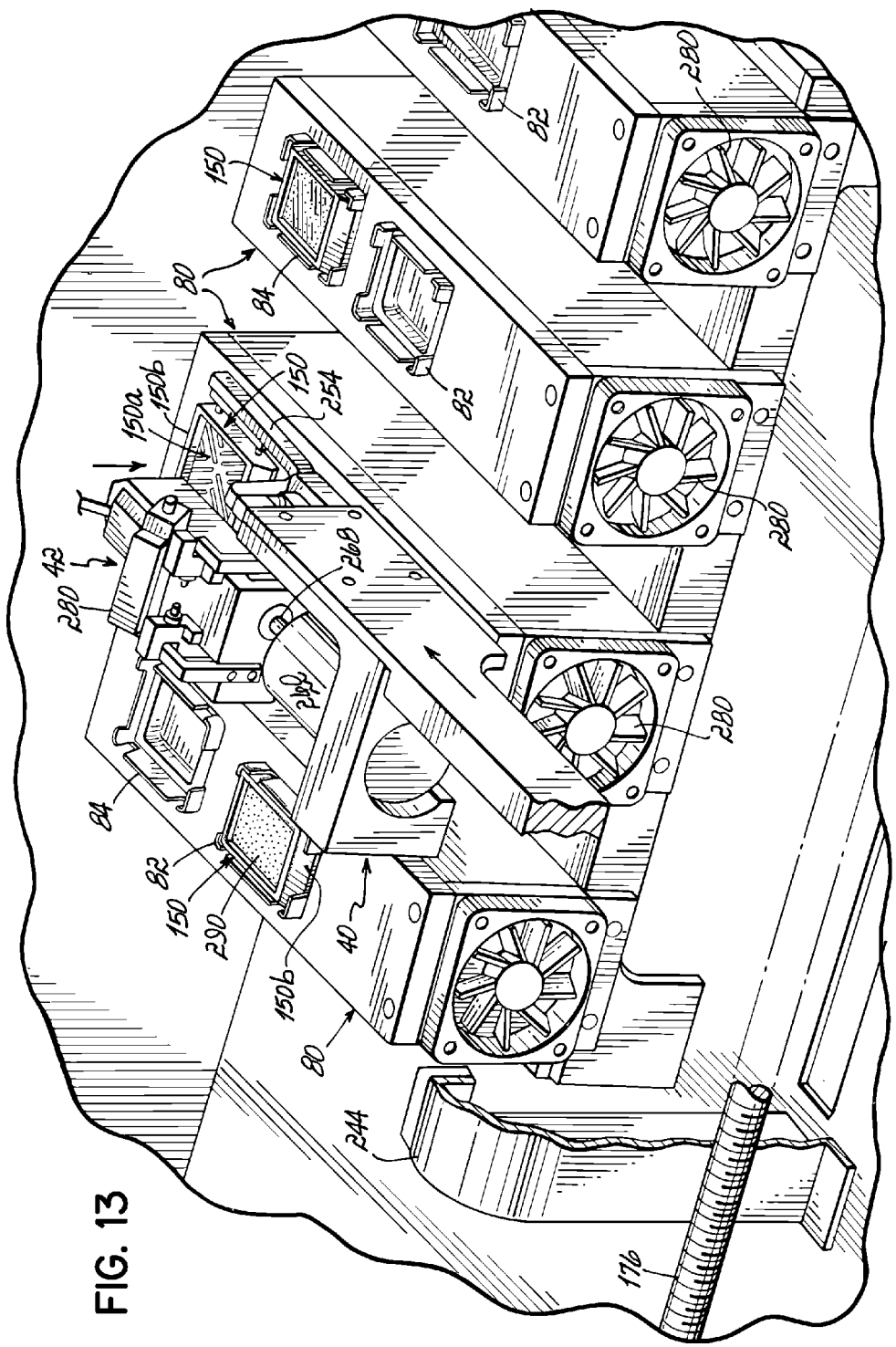
FIG. 13 is an enlarged perspective view showing the gripper assembly placing a cassette and frame assembly in a base mold associated with a thermal electric cooling (TEC) unit.

After the transport robot 40 has moved the gripper to the vertical clearance position, the control 352 executes, at 468, a load frame in mold subroutine illustrated in more detail in FIG. 23. First, the control 352 commands, at 632, the stepping motor 62a to lower the gripper 250 such that the frame and cassette assembly 150 is on or slightly above the mold 82a (FIG. 13). Thereafter, the control 352 commands, at 634, the gripper fingers 252 to open (FIG. 11A); and then, at 636, the control 352 reverses the operation of the stepping motor 62a to raise the gripper 250 to its vertical clearance position. The control then, at 638, reads the frame sensor 280 to confirm that a frame 150b is no longer present in the gripper 250. If a frame is detected, the control 352 displays an appropriate error signal, at 640, and ceases operation.

Figure 8:
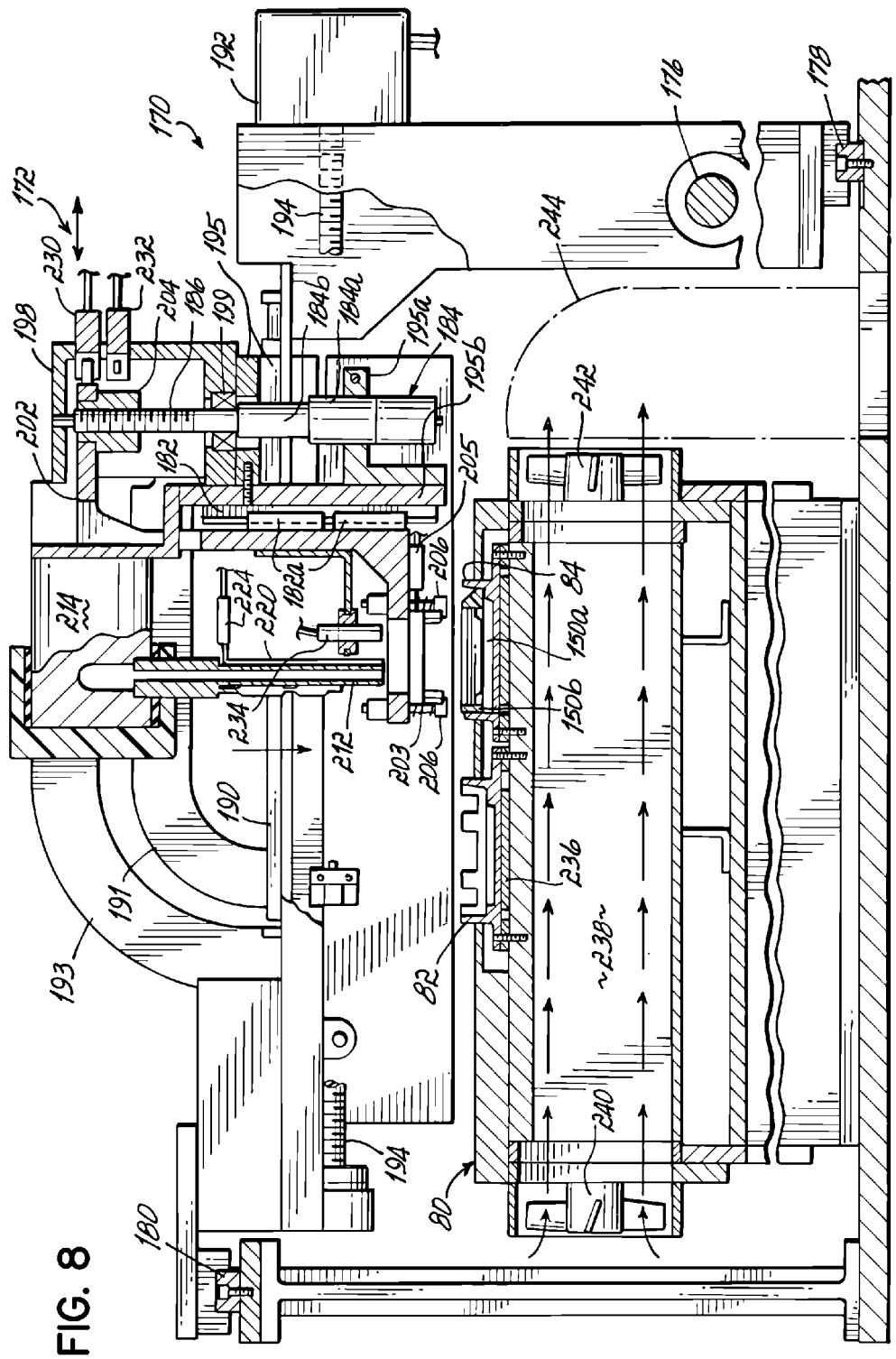
FIG. 8 is a cross sectional view taken generally along line 8-8 of FIG. 6.
Figure 9:
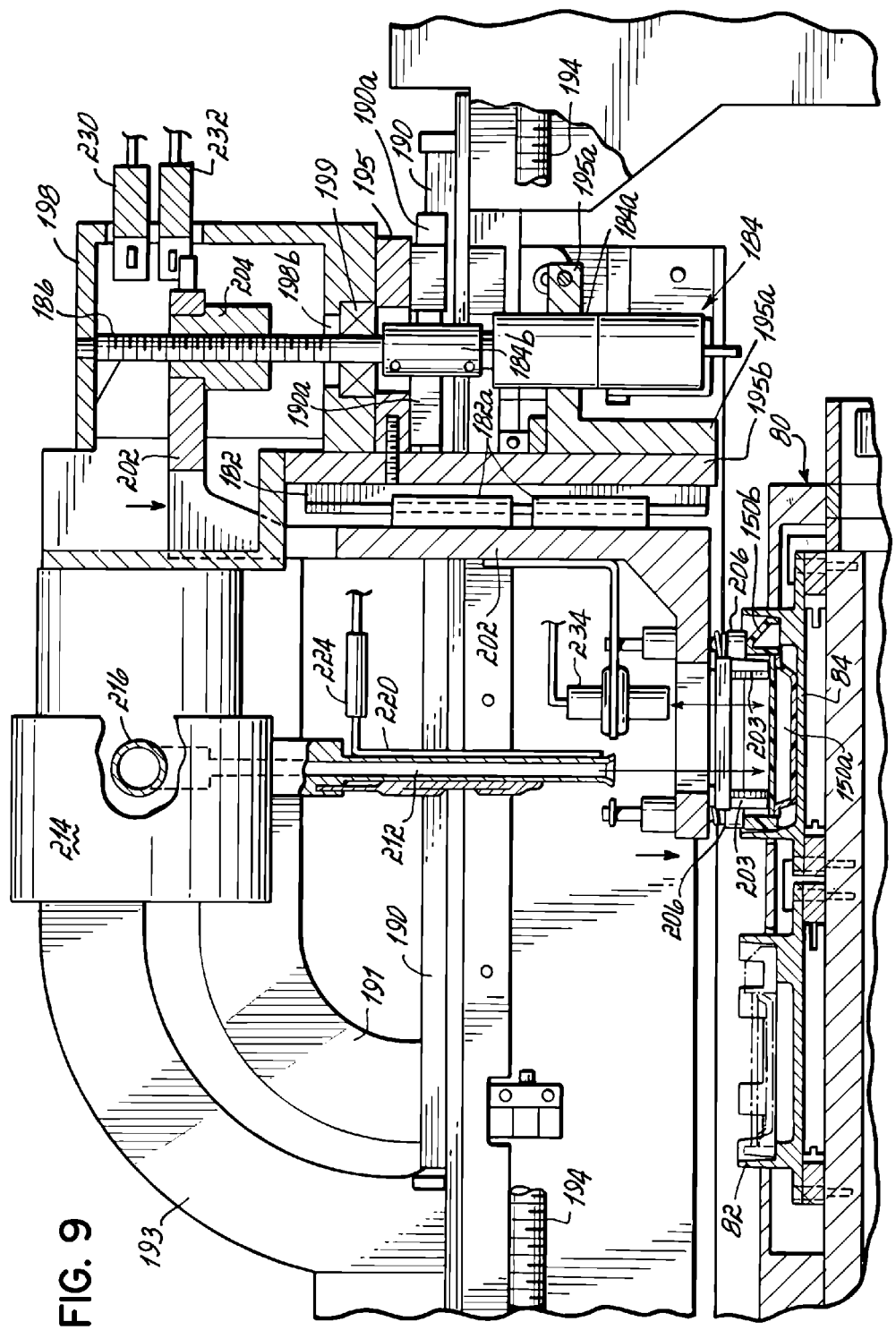
FIG. 9 is an enlarged cross sectional view similar to FIG. 8, but illustrating the staging of a cassette through its associated frame and into a base mold.
Figure 24:
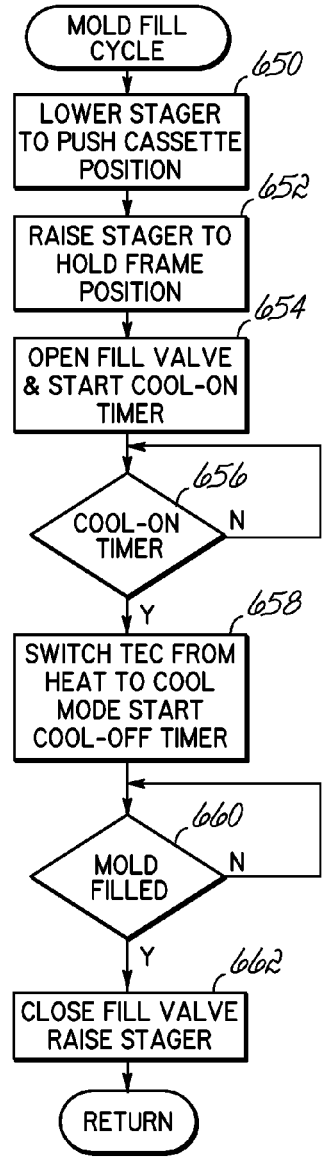
FIG. 24 is a flowchart illustrating a process executed by the control system of FIG. 17 to dispense paraffin into a mold in the machine of FIG. 1.

Next, the control 352 commands the stepper motor 174 to move the staging robot 170 over the mold. Thereafter, the control, at 472, starts an internal pause timer and then initiates, at 474, a mold fill cycle subroutine as shown in more detail in FIG. 24. In executing the mold fill cycle, the control 352 first commands, at 650, the stepper motor 184 to lower the stager/filler 172 (FIG. 8). The vertical support member 202 moves the four spring biased holding members 206 downwardly against the top corners of the frame 150b to immobilize the frame during the paraffin filling process. Simultaneously, the pushers 203 (FIG. 9) are moved downward against the top corner portions of the cassette 150a, thereby firmly pushing the cassette and frame assembly 150 firmly into the mold 84. The control 352 then commands, at 652, the motor 184 to raise the stager/filler 172 to a position at which the pushers 203 will not contact any paraffin during the filling process. It should be noted that the holding members 206 still retain the frame 150b against the mold with spring pressure. Thereafter, at 654, the control 352 provides an output signal to the solenoid driver 394 commanding the paraffin valve 214 to open and the mold to begin filling with paraffin (FIG. 10). In addition, the control 352 initiates the operation of an internal cool-on timer. It has been determined through experimentation that a higher quality process is achieved if the cooling of the mold is initiated slightly prior to the end of the mold filling cycle. However, the exact time that the TEC should be switched to a cool mode is application dependent. Therefore, after the control 352 determines, at 656, that the cool-on timer has expired; the control 352 switches, at 658, the operation of the respective TEC plate 236 from the heat mode to a cool mode and in addition, initiates the operation of an internal cool-off timer. The control 352 then determines, at 660, when it receives a signal from the paraffin fill sensor 234 indicating that the mold 84 is filled. At that point, the control 352 then provides, at 662, output signals to the solenoid driver 394 commanding the fill valve to close. In addition, the control 352 commands the stepper motor 184 to raise the stager/filler 172 to its uppermost position.

Returning to FIG. 20, upon initiating the mold fill cycle subroutine 476, the control 352 also determines whether the current mold being filled is the last mold to be filled. If not, the control then determines, at 454, whether the pause timer has expired. The pause timer simply causes the operation of the transport robot 40 to pause for a short period of time. If it has, the control then commands the stepper motors 60a, 62a, 64a to move the gripper to a position adjacent the opening of the basket. The process described with respect to steps 454-476 is repeated for each of the eight mold positions. When the last mold is being filled as detected at 476 by the control 352, the control then commands, at 478, the motor 60a to move the gripper 250 to the vertical clearance position over the first mold; and thereafter, the load molds cycle of FIG. 20 ends. It should be noted that, if at 460, the control 352 determines that a frame 150b is not present in the gripper 250, it then checks, at 480, whether the current basket is empty. The control 352 maintains a count of the frame and cassette assemblies 150 removed from the current basket. If a number of frame and cassette assemblies have been removed from the current basket equal to its maximum capacity, then the control, at 482, determines whether all baskets are empty. If not, the control commands the gripper then to move to the opening of the adjacent basket on the input door 16.

Figure 26:
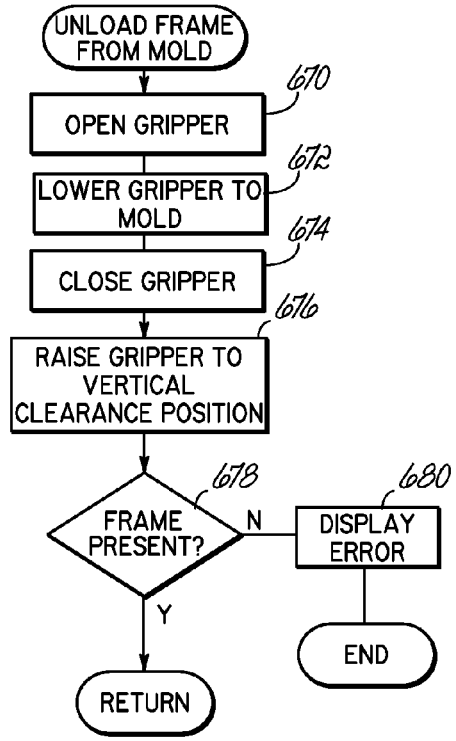
FIG. 26 is a flowchart illustrating a process executed by the control system of FIG. 17 to unload a frame and cassette assembly from a mold in the machine of FIG. 1.
Figure 25:
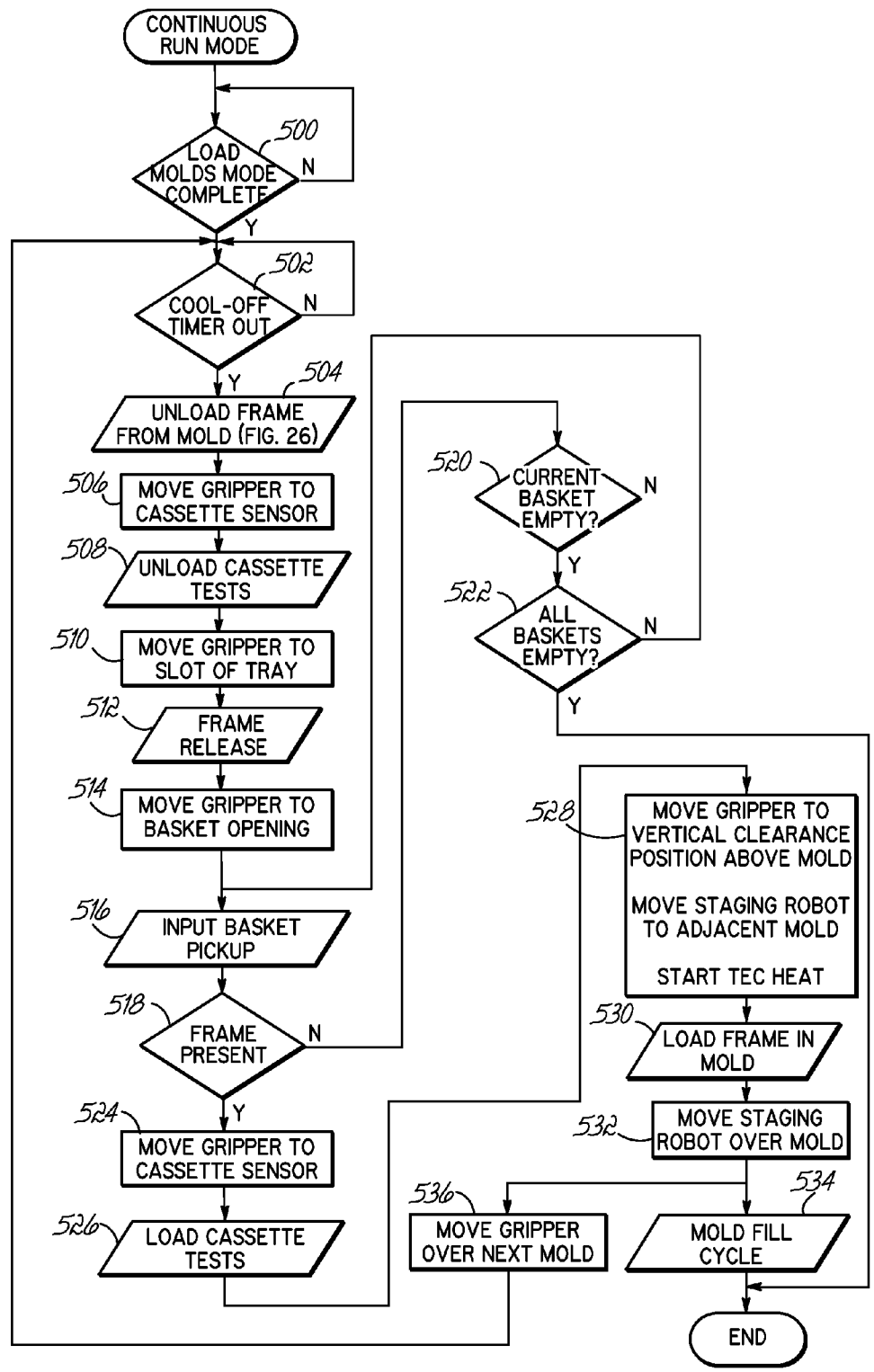
FIG. 25 is a flowchart illustrating a process executed by the control system of FIG. 17 to continuously load, fill and unload frame and cassette assemblies in the machine of FIG. 1.

After all the molds are initially filled with frame and cassette assemblies and fill cycles are initiated, the control 352 switches to a continuous run mode as illustrated in FIG. 25. The first step of that mode is to confirm, at 500, that the load molds mode is complete. It should be remembered that the transport robot 40 is currently positioned at the vertical clearance height above the first mold. The control 352 then determines, at 502, whether the cool-off timer for that mold has expired. When it does, the control then, at 504, executes an unload frame from mold subroutine illustrated in FIG. 26.

To unload a frame and cassette assembly from the mold 84, as shown in FIG. 14, the control 352 provides output signals at steps 670-676 to command the gripper fingers 252 to open, the stepper motor 64a to lower the gripper to the mold, the gripper fingers 252 to close and the stepper motor 62a to raise the gripper back to its vertical clearance position. Thereafter, the control 352 reads the state of the frame sensor 280 to determine whether a frame is present. If not, the control displays an error, at 680, and the cycle ends.

Figure 27:
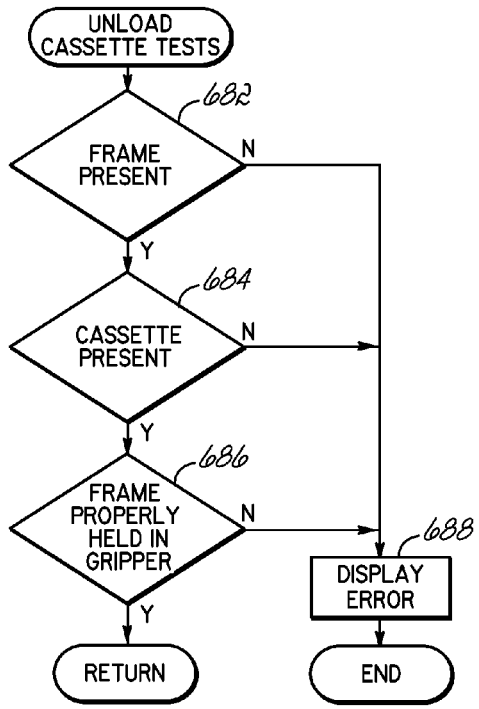
FIG. 27 is a flowchart illustrating a process executed by the control system of FIG. 17 to test a filled frame and cassette assembly removed from a mold in the machine of FIG. 1.

Referring back to FIG. 25, the control thereafter provides, at 506, command signals to the stepper motors 60a, 62a, 64a to move the gripper to the sensor 86 (FIG. 3). When in that position, the control 352 initiates, at 508, an unload cassette test subroutine shown in more detail in FIG. 27. First, the control 352 commands the stepper motors 60a, 62a, 64a to move the gripper 250 with respect to the sensor 86 such that by monitoring output signals from the sensor 86, the control 352 can determine, at 682, that a frame 150b is present. Thereafter, the control commands the gripper 250 to be moved to positions permitting the control 352 to determine, at 684, whether a cassette 150a is present in the frame. It is possible that in the filling and cooling process or in the unloading process, that the cassette became separated from the frame. It is also possible that the frame is not being properly held in the gripper. For example, referring to FIG. 11A, the frame 150b may be held by only the forward pins 252a, 254a of the gripper. In that scenario, the frame is slightly rotated such that the rearward pins 252b, 254b are not properly secured in the frame. To detect this situation, the control 352 commands the gripper 250 to be moved to positions permitting, at 686, the control to determine that the frame is properly secured in the gripper. If any error is detected, the control provides, at 688, an error display on the monitor 354 and the cycle ends.

Figure 28:
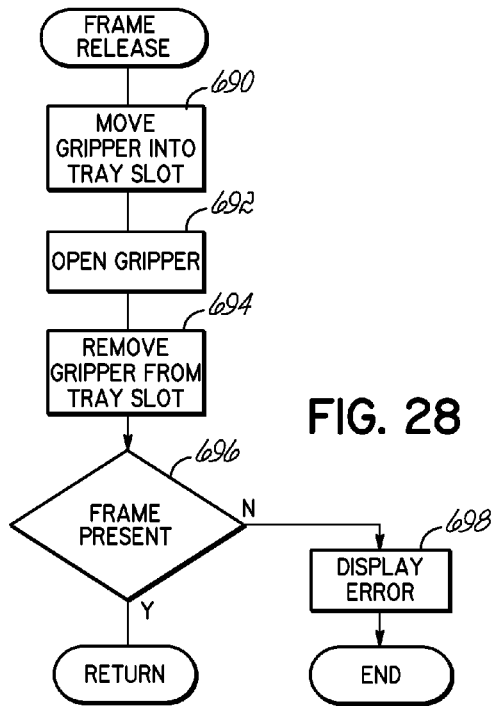
FIG. 28 is a flowchart illustrating a process executed by the control system of FIG. 17 to insert a filled frame and cassette assembly into an output tray in the machine of FIG. 1.

If the unload cassette test subroutine is successfully executed, returning to FIG. 25, the control 352 commands motors 60a, 62a, 64a to move the gripper with the cassette and frame assembly 150, now including a hardened block 290 of paraffin containing tissue sample 210, adjacent one of the slots 90 of one of the output trays 18a as shown in FIG. 15. Thereafter, the control 352 initiates a frame release subroutine illustrated in more detail in FIG. 28. To release the frame and cassette assembly 150, the control 352 first, at 690, commands the stepper motor 62a to move the gripper fingers 25 into the tray slot 90. The embedded cassette and frame assembly 150 is held within slot 90 by a spring loaded clip member 300 which frictionally engages the embedded cassette and frame assembly 150. Thereafter, at 692, the control commands the gripper fingers 252 to open and further commands the stepper motor 62a, at 694, to reverse motion, thereby removing the gripper fingers from the tray slot. Next, the control 352 reads the state of the frame sensor 280 to determine, at 696, whether a frame is present. If a frame is detected, the control 352 provides an error display to the monitor 354.

Figure 29:
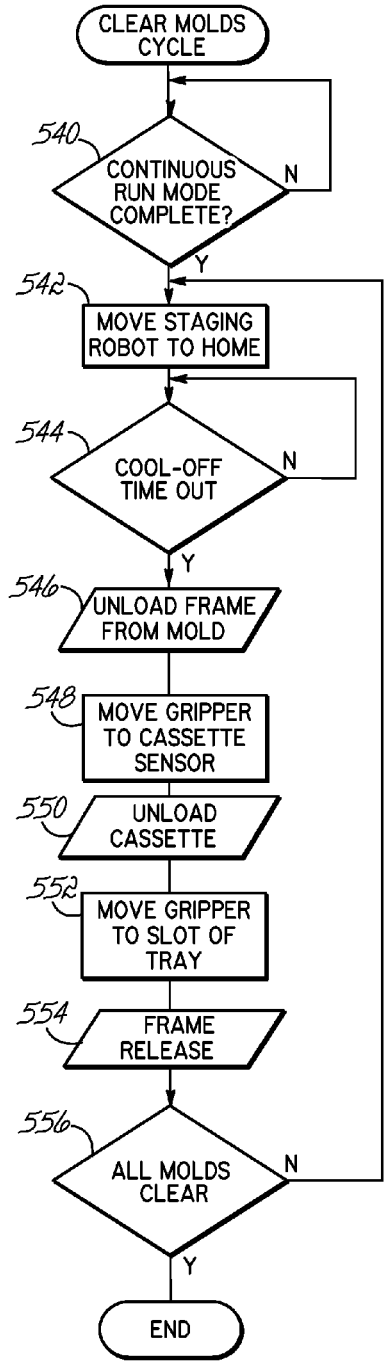
FIG. 29 is a flowchart illustrating a process executed by the control system of FIG. 17 to continuously transfer filled frame and cassette assemblies from the molds to the output trays in the machine of FIG. 1.

Returning to FIG. 25, the control then, at 514, provides command signals to the stepper motors 60a, 62a, 64a to move the gripper to a basket opening. The transport robot 40 then proceeds in response to commands from the control 352 to load another frame and cassette assembly from the input basket in accordance with steps 514-532. That loading operation is identical to the loading operation previously described with respect to steps 456 through 470 of FIG. 20. After loading another frame and cassette assembly 150 into the first mold, the control then, at 534, initiates a mold fill cycle as previously described with respect to FIG. 24. Simultaneously with initiating the mold fill cycle, the control 352 provides, at 536, a command signal to the stepper motor 60a to move the gripper over the next mold to be emptied. The controller then, at 502, determines whether the cool-off timer for that mold has expired. The process of steps 502-536 continues until the control 352 determines, at 522, that all the input baskets are empty. At that point, the continuous run mode ends and the control 352 switches to the clear molds cycle illustrated in FIG. 29.

After confirming, at 540, that the continuous run mode is complete, the control 352 commands, at 542, the stepper motors 174, 184 and 192 to move the staging robot to its home position. Thereafter, the control 352 determines, at 544, whether the cool-off timer for the current mold has expired. If so, the control 352 unloads a frame from that mold in accordance with process steps 546-554 that are identical to the process steps 504-512 previously described with respect to FIG. 25. That process iterates until the control 352 detects, at 556, that all molds are empty. At this point, the output trays can be removed from the machine 10. As shown in FIG. 16, output tray 18a may be removed by actuating solenoid 96, pivoting tray 18a outwardly, and lifting the tray 18a from the machine 10.

While the present invention has been illustrated by a description of a preferred embodiment and while the embodiment has been described in some detail, it is not the intention of Applicants to restrict or in any way limit the scope of the appended claims to such detail. Additional advantages and modifications will readily appear to those skilled in the art. The various features of the invention may be used alone or in numerous combinations depending on the needs and preferences of the user. For example, in the described embodiment, eight pairs of molds are used in order to accommodate cassettes of two different cassette sizes. As will be appreciated, in other embodiments, three different cassette sizes can be accommodated by providing 24 molds in a matrix of three molds in each of the eight rows of molds.

In the described embodiment, the sensor 86 is used to test the frame and cassette assemblies after being picked up from a basket and after being removed from a mold. As will be appreciated, another sensor can be placed in another location to test the frame and cassette assemblies after being removed from the mold. Such a different sensor may be desirable to improve the cycle time of the machine 10. As will be further appreciated, different types of sensors may change the process of checking the frame and cassette assemblies.

This has been a description of the present invention, along with the preferred methods of practicing the present invention as currently known. However, the invention itself should only be defined by the appended claims.

What is claimed is:

1. A method of processing tissue samples while the tissue samples are on liquid permeable tissue sample supports, and embedding the tissue samples on the liquid permeable tissue sample supports, comprising:
   loading a plurality of the liquid permeable tissue sample supports, each holding a tissue sample thereon, into an input member,
   placing the input member with the loaded liquid permeable tissue sample supports in a tissue processor,
   processing the tissue samples in the tissue processor to remove fluid from the tissue samples,
   introducing liquid embedding material into respective molds holding the liquid permeable tissue sample supports with the processed tissue samples while the input member is in an automated embedder,
   hardening the liquid embedding material in each mold with the tissue sample and associated liquid permeable tissue sample support, and
   removing the liquid permeable tissue sample supports and embedded tissue samples from the molds.

2. The method of claim 1, further comprising:
   holding the tissue samples between respective surfaces before the loading step, and
   continuing to hold the tissue samples between the respective surfaces during the steps of processing the tissue samples, introducing liquid embedding material and hardening the liquid embedding material.

3. The method of claim 2, further comprising holding the tissue samples between the respective surfaces such that each tissue sample is immobilized in a specific orientation during the steps of processing the tissue samples, introducing liquid embedding material and hardening the liquid embedding material.

4. The method of claim 1, wherein the liquid permeable tissue sample support further comprises a microtome sectionable support, and the method further comprises:
   after the removing step, sectioning through the hardened embedding material, the tissue sample and each microtome sectionable support in order to make sections for placement on microscope slides.

5. The method of claim 1, further comprising:
   after the removing step, sectioning through the hardened embedding material and each tissue sample in order to make sections for placement on microscope slides.

6. The method of claim 1, further comprising:
   transferring the input member holding the liquid permeable tissue sample supports and tissue samples from the tissue processor used for the tissue processing step to an automated embedder used for the step of introducing liquid embedding material.

7. The method of claim 6, wherein the transferring step is performed manually.

8. The method of claim 6, wherein the transferring step is performed by an automated mechanism.

9. A method of processing tissue samples while the tissue samples are on liquid permeable tissue sample supports, and embedding the tissue samples on the sample supports, comprising:
- loading a plurality of the liquid permeable tissue sample supports, each holding a tissue sample thereon, into an input member,
- placing the input member with the loaded liquid permeable tissue sample supports in a tissue processor,
- processing the tissue samples in the tissue processor to remove fluid from the tissue samples,
- introducing liquid embedding material into respective molds holding the liquid permeable tissue sample supports with the processed tissue samples while the input member is in an automated embedder,
- hardening the liquid embedding material in each mold with the tissue sample and associated liquid permeable tissue sample support, and
- removing the liquid permeable tissue sample supports and embedded tissue samples from the molds;

wherein the input member is perforated, and wherein processing the tissue samples further comprises directing tissue processing fluids through perforations in the input member in order to reach the tissue samples.

10. A method of processing tissue samples while the tissue samples are on liquid permeable tissue sample supports, and embedding the tissue samples on the sample supports, comprising:
- loading a plurality of the liquid permeable tissue sample supports, each holding a tissue sample thereon, into an input member, the input member including oppositely disposed sidewalls, each sidewall including at least one opening;
- placing the input member with the loaded liquid permeable tissue sample supports in a tissue processor;
- processing the tissue samples in the tissue processor to remove fluid from the tissue samples through the openings in the input member;
- introducing liquid embedding material into respective molds holding the liquid permeable tissue sample supports with the processed tissue samples while the input member is in an automated embedder;
- hardening the liquid embedding material in each mold with the tissue sample and associated liquid permeable tissue sample support; and
- removing the liquid permeable tissue sample supports and embedded tissue samples from the molds.

* * * * *